US012735663B2

(12) United States Patent
Takayama et al.

(10) Patent No.: US 12,735,663 B2

(45) Date of Patent: Sep. 15, 2026

(54) BILE DUCT CHIP AND USE THEREOF

(71) Applicants: Kyoto University, Kyoto (JP); OSAKA UNIVERSITY, Osaka (JP)

(72) Inventors: Kazuo Takayama, Kyoto (JP); Yusuke Torisawa, Kyoto (JP); Kenji Osafune, Kyoto (JP); Maki Kotaka, Kyoto (JP); Sayaka Deguchi, Kyoto (JP); Hiroyuki Mizuguchi, Osaka (JP)

(73) Assignees: KYOTO UNIVERSITY, Kyoto (JP); OSAKA UNIVERSITY, Osaka (JP)

( * ) Notice: Subject to any disclaimer, the term of this patent is extended or adjusted under 35 U.S.C. 154(b) by 530 days.

(21) Appl. No.: 18/280,659

(22) PCT Filed: Mar. 9, 2022

(86) PCT No.: PCT/JP2022/010191

§ 371 (c)(1),
(2) Date: Sep. 6, 2023

(87) PCT Pub. No.: WO2022/191222

PCT Pub. Date: Sep. 15, 2022

(65) Prior Publication Data

US 2024/0150691 A1 May 9, 2024

Related U.S. Application Data

(60) Provisional application No. 63/158,891, filed on Mar. 10, 2021.

(51) Int. Cl.

*C12M 3/00* (2006.01)
*C12M 1/00* (2006.01)
*C12M 3/06* (2006.01)

(52) U.S. Cl.

CPC ........... *C12M 21/08* (2013.01); *C12M 23/16* (2013.01); *C12M 29/04* (2013.01)

(58) Field of Classification Search

CPC ...... C12M 21/08; C12M 23/16; C12M 29/04; C12M 1/00

See application file for complete search history.

(56) References Cited

U.S. PATENT DOCUMENTS

2011/0250585 A1 10/2011 Ingber et al.
2018/0120298 A1 5/2018 Takezawa (Continued)

FOREIGN PATENT DOCUMENTS

CN 106754636 A 5/2017
JP 2011-528232 A 11/2011

(Continued)

OTHER PUBLICATIONS

Du et al., "A Bile Duct-on-a-Chip With Organ-Level Functions", Hepatology 71(4):1350-1363 (2020).

(Continued)

*Primary Examiner* — Jennifer Wecker
*Assistant Examiner* — Jonathan Bortoli
(74) *Attorney, Agent, or Firm* — Lathrop GPM LLP; Brian C. Trinque; Tanya D'Souza

(57) ABSTRACT

There is provided a bile duct chip that is a bile duct chip (200) including a membrane (210) through which substances are movable from one surface to the other surface, a first substrate (221) having a recessed part that forms a first flow path (220), and a second substrate (231) having a recessed part that forms a second flow path (230), in which the first substrate (221), the membrane (210), the second substrate (231) are stacked in this order, the recessed part of the first substrate (221) has an opening portion facing the one surface of the membrane (210), the recessed part of the second substrate has an opening portion facing the other surface of the membrane (210), the one surface of the membrane (210) forms a part of the first flow path (220), the other surface of (Continued)

the membrane (210) forms a part of the second flow path (230), the first flow path (220) and the second flow path (230) communicate with each other through the membrane (210), and bile duct epithelial cells (222) are disposed on a surface of an inner wall of the first flow path (220) to form a tube.

12 Claims, 23 Drawing Sheets

Specification includes a Sequence Listing.

(56) References Cited

U.S. PATENT DOCUMENTS

2019/0093077 A1* 3/2019 Hamilton ............... C12N 5/067
2020/0190456 A1* 6/2020 Huh ....................... C12M 23/34

FOREIGN PATENT DOCUMENTS

WO WO 2010/009307 A2 1/2010
WO WO 2013/086502 A1 6/2013
WO WO 2016/158417 A1 10/2016

OTHER PUBLICATIONS

Huh et al., "Reconstituting Organ-Level Lunch Functions on a Chip", Science 328:1662-1668 (2010).

International Search Report for International Application No. PCT/JP2022/010191 mailed May 17, 2022, 4 pages.

Takayama, "Optimization of device materials and cells for the development of liver-on-a-chip with liver function", The 20$^{th}$ Congress of Japanese Society for Regenerative Medicine Web Abstract, SY-10-2, p. 675 (2021).

* cited by examiner

FIG. 26

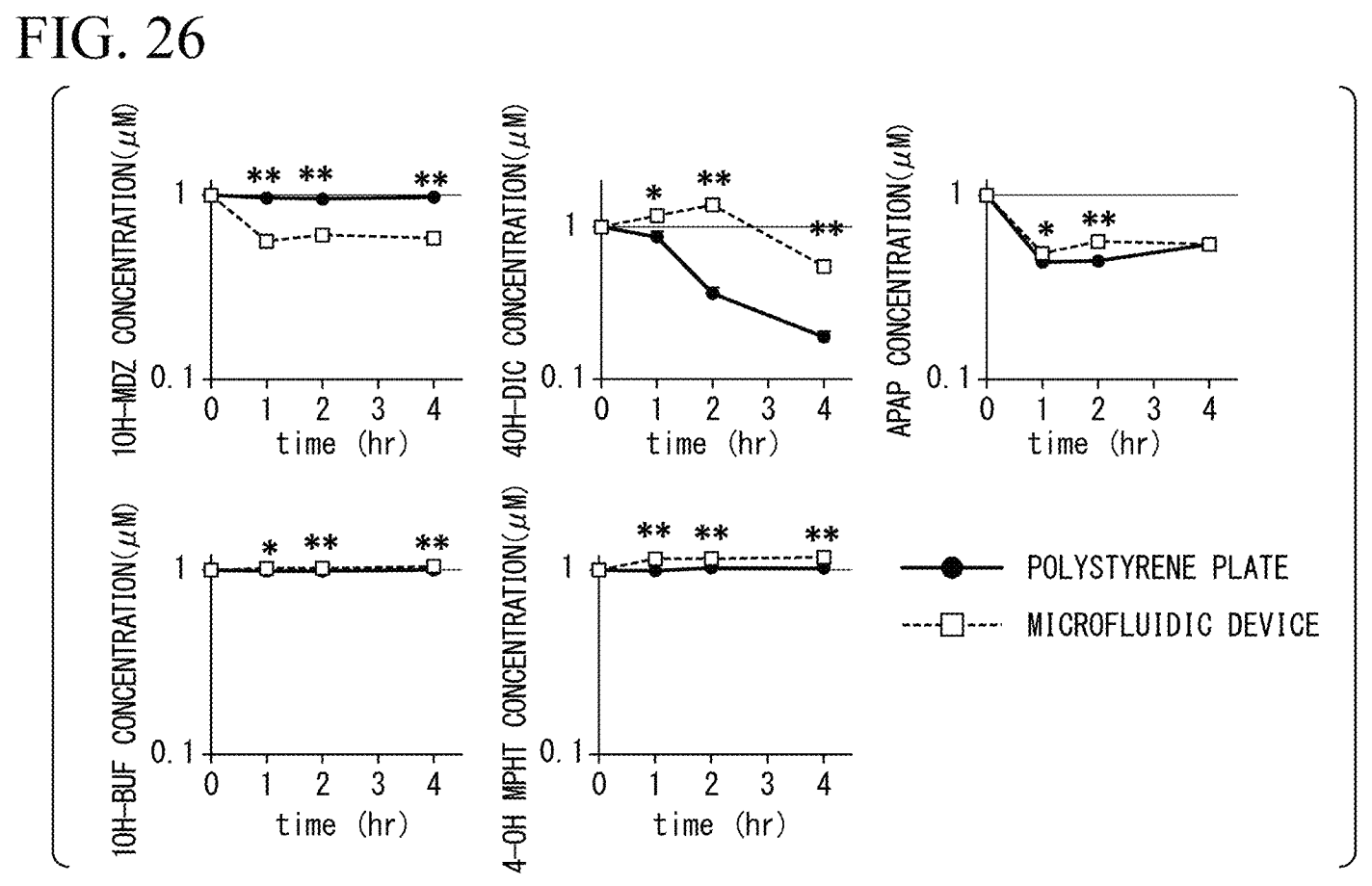

1OH-MDZ CONCENTRATION(μM)

4OH-DIC CONCENTRATION(μM)

APAP CONCENTRATION(μM)

1OH-BUF CONCENTRATION(μM)

4-OH MPHT CONCENTRATION(μM)

time (hr)

POLYSTYRENE PLATE

MICROFLUIDIC DEVICE

FIG. 29

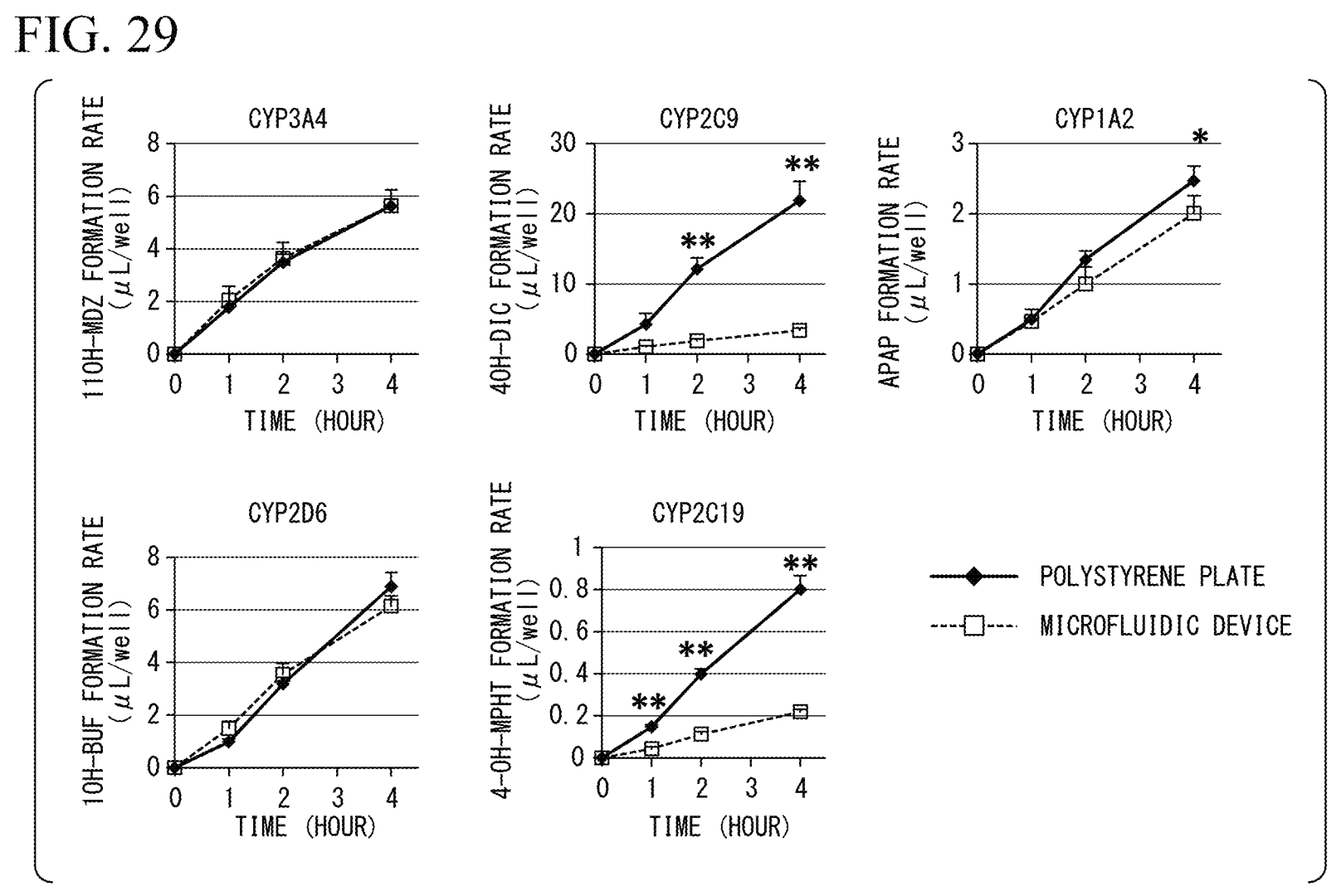

CYP3A4
11OH-MDZ FORMATION RATE (μL/well)
TIME (HOUR)

CYP2C9
4OH-DIC FORMATION RATE (μL/well)
TIME (HOUR)

CYP1A2
APAP FORMATION RATE (μL/well)
TIME (HOUR)

CYP2D6
1OH-BUF FORMATION RATE (μL/well)
TIME (HOUR)

CYP2C19
4-OH-MPHT FORMATION RATE (μL/well)
TIME (HOUR)

POLYSTYRENE PLATE
MICROFLUIDIC DEVICE

SEQUENCE LISTING

```
<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 1

gtggaaactt gcatggacaa c                                              21


<210> SEQ ID NO 2
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 2

aatcctggca catcgggaat c                                              21


<210> SEQ ID NO 3
<211> LENGTH: 22
<212> TYPE: DNA
<213> ORGANISM: Artificial Sequence
<220> FEATURE:
<223> OTHER INFORMATION: Synthesized oligonucleotide

<400> SEQUENCE: 3
```

```
gcacagaatc cttggtgaac ag                                              22


<210> SEQ ID NO 4
<211> LENGTH: 23
<212> TYPE: DNA
<213> ORGANISM: Artificial Sequence
<220> FEATURE:
<223> OTHER INFORMATION: Synthesized oligonucleotide

<400> SEQUENCE: 4

atggaaggtg aatgttttca gca                                             23


<210> SEQ ID NO 5
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 5

actgtcaact tcggggacac                                                 20


<210> SEQ ID NO 6
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 6

catgcctaaa cgcttcatca                                                 20


<210> SEQ ID NO 7
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 7

aagtcgcctc gaagatacac a                                               21


<210> SEQ ID NO 8
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 8

aaggagagaa cactgctcgt g                                               21


<210> SEQ ID NO 9
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 9

gagaaggcaa acgggtgaac                                                 20


<210> SEQ ID NO 10
<211> LENGTH: 23
<212> TYPE: DNA
```

<213> ORGANISM: Artificial Sequence
<220> FEATURE:
<223> OTHER INFORMATION: Synthesized oligonucleotide

<400> SEQUENCE: 10
gcacaacacc ttatggtatg aca 23

<210> SEQ ID NO 11
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 11
tgatcctgat caagggaagg 20

<210> SEQ ID NO 12
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 12
tggttcctgg gaaacaattc 20

<210> SEQ ID NO 13
<211> LENGTH: 22
<212> TYPE: DNA
<213> ORGANISM: Artificial Sequence
<220> FEATURE:
<223> OTHER INFORMATION: Synthesized oligonucleotide

<400> SEQUENCE: 13
tgagcaagtt tgaaacgcac at 22

<210> SEQ ID NO 14
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 14
agctcttctc ctgccgtctc t 21

<210> SEQ ID NO 15
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 15
gtcccaggtg taccgtgaag 20

<210> SEQ ID NO 16
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 16 ccctttttggg aaaccttctg 20

<210> SEQ ID NO 17
<211> LENGTH: 19
<212> TYPE: DNA
<213> ORGANISM: Artificial Sequence
<220> FEATURE:
<223> OTHER INFORMATION: Synthesized oligonucleotide

<400> SEQUENCE: 17
agaaggtgga gcaggtggt 19

<210> SEQ ID NO 18
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 18
atcttggtct gtggctgctc 20

<210> SEQ ID NO 19
<211> LENGTH: 23
<212> TYPE: DNA
<213> ORGANISM: Artificial Sequence
<220> FEATURE:
<223> OTHER INFORMATION: Synthesized oligonucleotide

<400> SEQUENCE: 19
ggtggtctcc tctgacttca aca 23

<210> SEQ ID NO 20
<211> LENGTH: 19
<212> TYPE: DNA
<213> ORGANISM: Artificial Sequence
<220> FEATURE:
<223> OTHER INFORMATION: Synthesized oligonucleotide

<400> SEQUENCE: 20
gtggtcgttg agggcaatg 19

<210> SEQ ID NO 21
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 21
attaaccctg ctcggtcctt 20

<210> SEQ ID NO 22
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 22
accctggagt tgatgtcgtc 20

<210> SEQ ID NO 23
<211> LENGTH: 20
<212> TYPE: DNA
<213> ORGANISM: Artificial Sequence
<220> FEATURE:

<223> OTHER INFORMATION: Synthesized oligonucleotide

<400> SEQUENCE: 23
ctcccgcgac tacagccact 20

<210> SEQ ID NO 24
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 24
tcagctcatc cagcaccctg 20

<210> SEQ ID NO 25
<211> LENGTH: 22
<212> TYPE: DNA
<213> ORGANISM: Artificial Sequence
<220> FEATURE:
<223> OTHER INFORMATION: Synthesized oligonucleotide

<400> SEQUENCE: 25
ttggaaccag atgcacattg at 22

<210> SEQ ID NO 26
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 26
tcttgcgact cacgcttgac 20

<210> SEQ ID NO 27
<211> LENGTH: 22
<212> TYPE: DNA
<213> ORGANISM: Artificial Sequence
<220> FEATURE:
<223> OTHER INFORMATION: Synthesized oligonucleotide

<400> SEQUENCE: 27
aacagtgttg acatgaagag cc 22

<210> SEQ ID NO 28
<211> LENGTH: 22
<212> TYPE: DNA
<213> ORGANISM: Artificial Sequence
<220> FEATURE:
<223> OTHER INFORMATION: Synthesized oligonucleotide

<400> SEQUENCE: 28
tgtaaaacag cacgtcatcc tt 22

<210> SEQ ID NO 29
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 29
agagtggagc ctggtcttac a 21

<210> SEQ ID NO 30
<211> LENGTH: 23
<212> TYPE: DNA
<213> ORGANISM: Artificial Sequence
<220> FEATURE:
<223> OTHER INFORMATION: Synthesized oligonucleotide

<400> SEQUENCE: 30
cctttgctga caataagcac tgg 23

<210> SEQ ID NO 31
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 31
aaaagacagc tacgtgggtg a 21

<210> SEQ ID NO 32
<211> LENGTH: 22
<212> TYPE: DNA
<213> ORGANISM: Artificial Sequence
<220> FEATURE:
<223> OTHER INFORMATION: Synthesized oligonucleotide

<400> SEQUENCE: 32
gccatgttct atcgggtact tc 22

<210> SEQ ID NO 33
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 33
gagggccaag acgaagacat c 21

<210> SEQ ID NO 34
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 34
cagatcacgt catcgcacaa c 21

<210> SEQ ID NO 35
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 35
caatcaggtg gtggtgtcag 20

<210> SEQ ID NO 36
<211> LENGTH: 20
<212> TYPE: DNA
<213> ORGANISM: Artificial Sequence
<220> FEATURE:
<223> OTHER INFORMATION: Synthesized oligonucleotide -continued

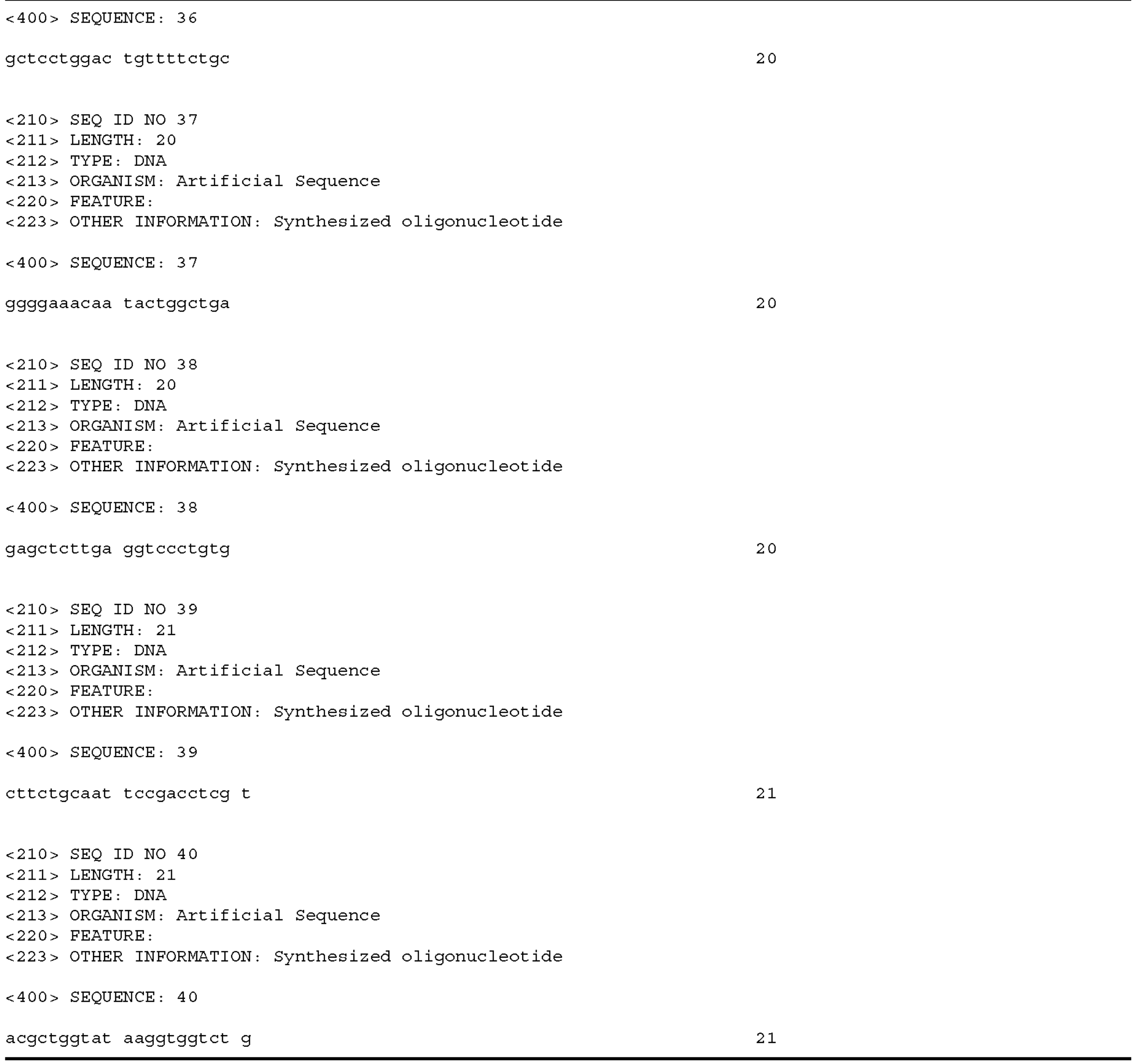

<400> SEQUENCE: 36
gctcctggac tgttttctgc 20

<210> SEQ ID NO 37
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 37
ggggaaacaa tactggctga 20

<210> SEQ ID NO 38
<211> LENGTH: 20
<212> TYPE: DNA
<213> ORGANISM: Artificial Sequence
<220> FEATURE:
<223> OTHER INFORMATION: Synthesized oligonucleotide

<400> SEQUENCE: 38
gagctcttga ggtccctgtg 20

<210> SEQ ID NO 39
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 39
cttctgcaat tccgacctcg t 21

<210> SEQ ID NO 40
<211> LENGTH: 21
<212> TYPE: DNA
<213> ORGANISM: Artificial Sequence
<220> FEATURE:
<223> OTHER INFORMATION: Synthesized oligonucleotide

<400> SEQUENCE: 40
acgctggtat aaggtggtct g 21

BILE DUCT CHIP AND USE THEREOF

TECHNICAL FIELD

The present invention relates to a bile duct chip and a use thereof. More specifically, the present invention relates to a bile duct chip, a producing method for a bile duct chip, and a method for evaluating bile acid kinetics. Priority is claimed on Provisional Application No. U.S. 63/158,891 provisionally filed to the United States on Mar. 10, 2021, the content of which is incorporated herein by reference.

SEQUENCE LISTING

The instant application contains a Sequence Listing which has been submitted electronically in TXT format and is hereby incorporated by reference in its entirety. Said ASCII file, created on Sep. 6, 2023, is named 746214_SGT-030US_ST25.txt and is 8,287 bytes in size.

BACKGROUND ART

In the liver, hepatocytes synthesize bile acid. The synthesized bile acid is discharged into the bile canaliculus, via a hepatic transporter, and flows into the intrahepatic bile duct. Then, the bile acid is secreted into the gastrointestinal tract via the extrahepatic bile duct. Although bile acid plays an important role in lipid metabolism and the like, an excessive amount of bile acid is toxic to hepatocytes. Therefore, cholestatic liver damage is caused in a case where the kinetics of bile acid is inhibited and bile acid is accumulated in hepatocytes. The cholestatic liver damage is a disease associated with a risk of hepatic cirrhosis or hepatic cancer.

Approximately 40% of the drug-induced liver damages are classified into the cholestatic type. In addition, it is known that some gene mutations cause the cholestatic liver damage. In order to study the cholestatic liver damage and develop a therapeutic drug, a model capable of reproducing the kinetics of bile acid is required. In addition, a model of reproducing the kinetics of bile acid is also important for identifying drug candidate compounds that cause the cholestatic liver damage at an early stage of drug development.

In general, hepatocytes cultured on a 2D cell culture plate are used as an in vitro liver model. In the 2D hepatocyte model, there is a bile canaliculus between adjacent hepatocytes, and it is possible to reproduce the flow of bile from the hepatocytes to the bile canaliculus. However, since the 2D hepatocyte model does not have an intrahepatic bile duct composed of bile duct cells, it is not possible to reproduce the flow of bile from the bile canaliculus to the intrahepatic bile duct. For this reason, it is difficult to reproduce the kinetics of bile acid in vitro using the 2D hepatocyte model.

An Organ-on-a-chip technique is a technique that makes it possible to partially reproduce organ functions in vitro by culturing cells in a microfluidic device (see, for example, Patent Document 1). The performance of the Organ-on-a-chip is greatly influenced by the cells to be mounted and the materials used for the microfluidic device. As hepatocytes to be mounted on a Liver-on-a-chip, human primary cultured hepatocytes are most widely used. However, in order to produce an in vitro liver model that can mimic the kinetics of bile acid, it is indispensable to use not only human primary cultured hepatocytes but also non-parenchymal cells such as bile duct epithelial cells.

CITATION LIST

Patent Document

[Patent Document 1]
United States Patent Application, Publication No. 2011/0250585

SUMMARY OF INVENTION

Technical Problem

In a case of reproducing a bile duct structure in vitro, spherical cysts are often constructed in a collagen gel. Recently, an example in which a spherical bile duct organoid is developed from CK19, SOX9, or LGR5-positive cells that appear at the time of liver damage has been reported. However, in any of the above techniques, only a spherical bile duct-like structure has been produced, and an example in which a tubular bile duct-like structure is successfully produced has not been known. A technical issue which makes it difficult to produce a tubular bile duct includes a fact that the migration ability of bile duct epithelial cells constituting the bile duct is low. An object of the present invention is to provide a bile duct chip having a tubular bile duct-like structure.

Solution to Problem

The present invention includes the following aspects.

[1] A bile duct chip including:

a membrane through which substances are movable from one surface to the other surface;

a first substrate having a recessed part that forms a first flow path; and a second substrate having a recessed part that forms a second flow path, in which the first substrate, the membrane, and the second substrate are stacked in this order, the recessed part of the first substrate has an opening portion facing the one surface of the membrane, and the recessed part of the second substrate has an opening portion facing the other surface of the membrane, the one surface of the membrane forms a part of the first flow path, the other surface of the membrane forms a part of the second flow path, and the first flow path and the second flow path communicate with each other through the membrane, and bile duct epithelial cells are disposed on a surface of an inner wall of the first flow path to form a tube.

[2] The bile duct chip according to [1], in which second cells are disposed in the second flow path, and the second cells are adjacent to the bile duct epithelial cells across the membrane.

[3] The bile duct chip according to [2], in which the second cells include any one or more kinds of cells selected from the group consisting of liver cells and intestinal cells.

[4] The bile duct chip according to [3], in which the second cells are the liver cells, and the tube is a model of an intrahepatic bile duct.

[5] A producing method for a bile duct chip, including:

a step of seeding bile duct epithelial cells in a first flow path of a microfluidic device which includes a membrane through which substances are movable from one surface to the other surface, a first substrate having a recessed part that forms the first flow path, and a second substrate having a recessed part that forms a second flow path, where the first substrate, the membrane, and the second substrate are stacked in this order, the recessed part of the first substrate has an opening portion facing the one surface of the membrane, the recessed part of the second substrate has an opening portion facing the other surface of the membrane, the one surface of the membrane forms a part of the first flow path, the other surface of the membrane forms a part of the second flow path, and the first flow path and the second flow path communicate with each other through the membrane; and a step of introducing a culture medium containing a lumenization factor into the first flow path.

[6] The producing method according to [5], in which the lumenization factor is any one or more kinds of factors selected from the group consisting of Delta Like Canonical Notch Ligand 1 (DLL1) and Delta Like Canonical Notch Ligand 4 (DLL4).

[7] The producing method according to [6], in which the lumenization factor is DLL1.

[8] The producing method according to any one of [5] to [7], further including a step of seeding second cells in the second flow path after the bile duct epithelial cells are disposed on a surface of an inner wall of the first flow path to form a tube, in which the second cells are adjacent to the bile duct epithelial cells across the membrane.

[9] The producing method according to [8], in which the second cells include any one or more kinds of cells selected from the group consisting of liver cells and intestinal cells.

[10] The producing method according to [9], in which the second cells are the liver cells, and the tube is a model of an intrahepatic bile duct.

[11] A method for evaluating bile acid kinetics, the method including:

a step of adding a test substance into a first flow path or a second flow path of a bile duct chip which includes a membrane through which substances are movable from one surface to the other surface, a first substrate having a recessed part that forms the first flow path, and a second substrate having a recessed part that forms the second flow path, where the first substrate, the membrane, and the second substrate are stacked in this order, the recessed part of the first substrate has an opening portion facing the one surface of the membrane, the recessed part of the second substrate has an opening portion facing the other surface of the membrane, the one surface of the membrane forms a part of the first flow path, the other surface of the membrane forms a part of the second flow path, the first flow path and the second flow path communicate with each other through the membrane, bile duct epithelial cells are disposed on a surface of an inner wall of the first flow path to form a tube, and liver cells are disposed in the second flow path; and a step of measuring an abundance of bile acid in the first flow path or the second flow path, or an expression level of a gene or a protein, which is associated with bile acid kinetics in the bile duct epithelial cells or the liver cells.

[12] The method according to [11], in which the bile acid kinetics is kinetics of one or more kinds of factors selected from the group consisting of an in vivo compound other than bile acid, a drug, and a pathogen, and bile acid.

Advantageous Effects of Invention

According to the present invention, it is possible to provide a bile duct chip having a tubular bile duct-like structure.

BRIEF DESCRIPTION OF DRAWINGS

FIG. 2(*b*) is a perspective view showing a structure of a bile duct chip according to one embodiment. FIG. 2(*c*) is an enlarged schematic view of a portion surrounded by a square in FIG. 2(*b*).

FIG. 26 shows graphs showing results of quantifying drugs in Experimental Example 7.

FIG. 29 shows graphs showing results of measuring metabolites of drugs in Experimental Example 9.

DESCRIPTION OF EMBODIMENTS

Abbreviation

In the present specification, the following abbreviations may be used.

Microphysiological systems: MPS, Liver-on-a-chip model: liver-chip, primary human hepatocytes: PHH, Polydimethylsiloxane: PDMS, (PDMS-based microfluidic device: PDMS device), cytochrome P450: CYP, Polystyrene: PS, polyethylene terephthalate: PET, albumin: ALB, cytokeratin 18: CK18, midazolam: MDZ, diclofenac: DIC, phenacetin: PHE, bufuralol: BUF, S-mephenytoin: MPHT, 1-hydroxymidazolam: 1OH-MDZ, 4-hydroxydiclofenac: 4OH-DIC, acetaminophen: APAP, 1-hydroxybufuralol: 1OH-BUF, 4-hydroxymephenytoin: 4OH-MPHT, diffusion coefficients: DiffCoef, molecular weight: MWt, topological polar surface area: tPSA, atorvastatin (ATV), 2-hydroxyatorvastatin: 2OH-ATV, chenodeoxycholic acid: CDCA, transforming growth factor β1: TGF-β1, human umbilical vein endothelial cell: HUVEC, and tetrafluoroethylene-propylene: FEPM

[Bile Duct Chip]

In one embodiment, the present invention provides a bile duct chip. The bile duct chip according to the present embodiment includes a membrane through which substances are movable from one surface to the other surface, a first substrate having a first recessed part that forms a first flow path, and a second substrate having a second recessed part that forms a second flow path, where the first substrate, the membrane, and the second substrate are stacked in this order, the first recessed part of the first substrate has an opening portion facing the one surface of the membrane, the second recessed part of the second substrate has an opening portion facing the other surface of the membrane, the one surface of the membrane forms a part of the first flow path, the other surface of the membrane forms a part of the second flow path, the first flow path and the second flow path communicate with each other through the membrane, bile duct epithelial cells are disposed on a surface of an inner wall of the first flow path to form a tube. As will be described later in Examples, the bile duct chip according to the present embodiment has a tubular bile duct-like structure.

Figure 1:
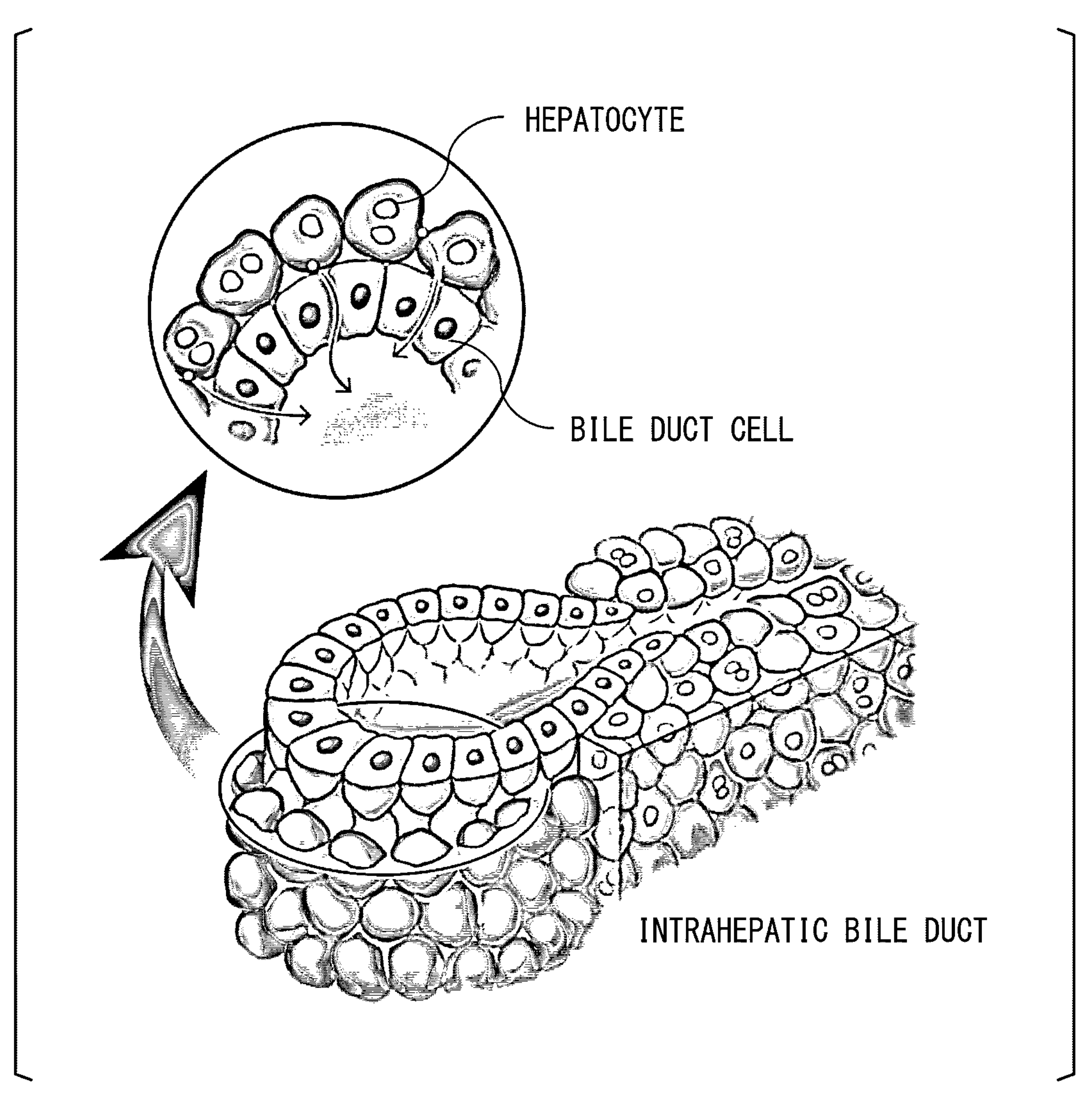
FIG. 1 is a schematic view showing a structure of an intrahepatic bile duct in vivo.
Figure 2:
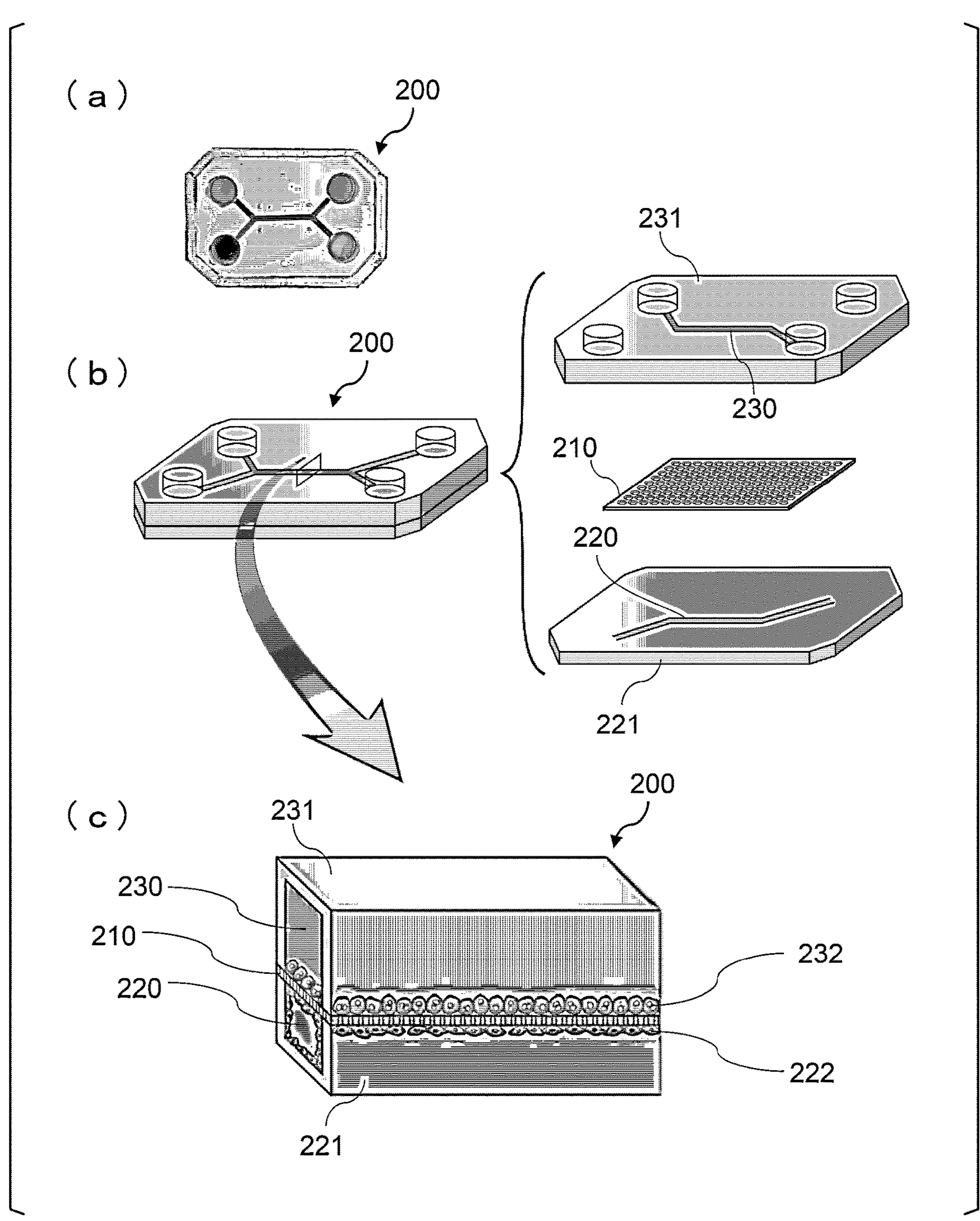
FIG. 2(*a*) is a plan view (a photographic image) of a bile duct chip according to one embodiment.

FIG. 1 is a schematic view showing a structure of an intrahepatic bile duct in vivo. The bile duct chip according to the present embodiment can mimic, for example, an intrahepatic bile duct in vivo. FIG. 2(*a*) is a plan view (a photographic image) of a bile duct chip according to the present embodiment. FIG. 2(*b*) is a perspective view showing a structure of the bile duct chip according to the present embodiment. FIG. 2(*c*) is an enlarged schematic view of a portion surrounded by a square in FIG. 2(*b*).

As shown in FIG. 2(*c*), a bile duct chip 200 includes a membrane 210 through which substances are movable from one surface to the other surface, a first substrate 221 having a first recessed part that forms a first flow path 220, and a second substrate 231 having a second recessed part that forms a second flow path 230, where the first substrate 221, the membrane 210, the second substrate 231 are stacked in this order, the first recessed part of the first substrate 221 has an opening portion facing the one surface of the membrane 210, the second recessed part of the second substrate 231 has an opening portion facing the other surface of the membrane 210, the one surface of the membrane 210 forms a part of the first flow path 220, the other surface of the membrane 210 forms a part of the second flow path 230, the first flow path 220 and the second flow path 230 communicate with each other through the membrane 210, and bile duct epithelial cells 222 are disposed on a surface of an inner wall of the first flow path 220 to form a tube.

In the present specification, the recessed part refers to a portion that is recessed from the reference surface. In the first substrate 221, the reference surface is a surface of the first substrate 221 facing the membrane 210. In the bile duct chip according to the present embodiment, the first recessed part (groove) formed in the first substrate 221 serves as the wall of the first flow path 220. Similarly, the second recessed part (groove) formed in the second substrate (231) serves as the wall of the second flow path 230.

The membrane 210 may be a monolayered membrane or may be a membrane in which two or more layers are stacked. In a case where a plurality of membranes are stacked, the one surface of the membrane 210 means a surface on which the opening portion of the first recessed part of the membrane 210 that is closest to the first substrate 221 is faced. In addition, in a case where a plurality of membranes are stacked, the other surface of the membrane 210 means a surface on which the opening portion of the second recessed part of the membrane 210 that is closest to the second substrate 231 is faced.

A width of a cross section of each of the first flow path 220 and the second flow path 230 may be about 100 μm to 10 mm, and the height thereof may be about 30 μm to 3 mm. In addition, the length of each of the first flow path 220 and the second flow path 230 can be appropriately adjusted depending on the intended purpose; however, it may be, for example, about 1 mm to 100 mm.

It is preferable that an introduction port and a discharge port for introducing and discharging cells or a culture medium into the flow path are at an end part of the first flow path 220. Similarly, it is preferable that an introduction port and a discharge port for introducing and discharging cells or a culture medium into the flow path are at an end part of the second flow path 230.

Hereinafter, the bile duct chip before seeding cells may be referred to as a microfluidic device. In addition, the first flow path 220 may be referred to as a lower layer flow path, and the second flow path 230 may be referred to as an upper layer flow path.

An elastomer can be preferably used as a material of the first substrate 221 and the second substrate 231, and more specific examples thereof include polydimethylsiloxane (PDMS) and tetrafluoroethylene-propylene (FEPM), which are not limited thereto. PDMS is easy to be molded, has high transparency, and thus is suitable for cell observation. However, as will be described later in Examples, PDMS is highly hydrophobic and thus may absorb drugs. On the other hand, FEPM is capable of inhibiting the absorption of drugs.

As the membrane 210, a semi-permeable membrane having a pore size of about 0.01 to 80 μm can be preferably used. The material of the membrane 210 is not particularly limited, and examples thereof include polyethylene terephthalate (PET), collagen Vitrigel, and polycarbonate (PC). The membrane 210 may be a monolayered semi-permeable membrane or may be a semi-permeable membrane in which two or more layers are stacked.

In the bile duct chip according to the present embodiment, second cells 232 may be disposed in the second flow path 230, and the second cells 232 may be adjacent to the bile duct epithelial cells 222 across the membrane 210. In addition, the second cells 232 may include any one or more kinds of cells selected from the group consisting of liver cells and intestinal cells.

In a case where the second cells 232 are liver cells, the above-described tube serves as a model that mimics an intrahepatic bile duct in vivo. The hepatocytes are preferably liver cells (parenchymal cells). In this case, it can be said that the bile duct chip according to the present embodiment is an intrahepatic bile duct chip. As will be described later in Examples, according to the intrahepatic bile duct chip, bile acid produced by the hepatocyte 232 in the second flow path 230 is transported into a tubular bile duct-like structure formed by the bile duct epithelial cells 222 in the first flow path 220. That is, the intrahepatic bile duct chip makes it possible to observe the directional transport of bile acid. In addition, it is also possible to evaluate the cholestatic effect of the drug. In a case where bile acid is not properly excreted into the bile duct and remains in the hepatocytes, cholestasis occurs. In a case of using the intrahepatic bile duct chip, it is possible to easily find a drug having a possibility of causing cholestasis.

In a case where the second cells 232 are intestinal cells, a drug added to the second flow path is metabolized by the intestinal cells and then transported into the first flow path. That is, the metabolism and the transport of the drug can be observed. The intestinal cells are preferably intestinal epithelial cells.

The liver cells and the intestinal cells may be primary cells, may be established cells, or may be cells obtained by being induced to differentiate from pluripotent stem cells. Examples of the pluripotent stem cell include an embryonic stem cell (ESC) and an induced pluripotent stem cell (iPSC).

As will be described later in Examples, the inventors of the present invention evaluated drug absorption into a microfluidic device made of PDMS. As a result, it was revealed that the absorption rate of the drug correlates with the distribution coefficient (S+Log D value) of the drug ($R^2$=0.71). In addition, it was revealed that a large number of drugs with S+log D<2 are hardly absorbed by the microfluidic device made of PDMS. Therefore, in a case where a drug is evaluated using an intrahepatic bile duct chip made of PDMS, a drug with S+log D<2 may be preferable since the absorption of the drug into a microfluidic device is small

[Producing Method for Bile Duct Chip]

In one embodiment, the present invention provides a producing method for a bile duct chip, including a step of seeding bile duct epithelial cells in a first flow path of a microfluidic device which includes a membrane through which substances are movable from one surface to the other surface, a first substrate having a first recessed part that forms a first flow path, and a second substrate having a second recessed part that forms a second flow path, where the first substrate, the membrane, and the second substrate are stacked in this order, the first recessed part of the first substrate has an opening portion facing the one surface of the membrane, the second recessed part of the second substrate has an opening portion facing the other surface of the membrane, the one surface of the membrane forms a part of the first flow path, the other surface of the membrane forms a part of the second flow path, and the first flow path and the second flow path communicate with each other through the membrane; and a step of introducing a culture medium containing a lumenization factor into the first flow path.

The bile duct chip 200 described above can be produced by the producing method according to the present embodiment. In a description with reference to FIG. 2(*c*), the producing method according to the present embodiment include a step of seeding the bile duct epithelial cells 222 in the first flow path 220 of the microfluidic device 200 including a membrane 210 through which substances are movable from one surface to the other surface, a first substrate 221 having a first recessed part that forms a first flow path 220, and a second substrate 231 having a second recessed part that forms a second flow path 230, where the first substrate 221, the membrane 210, the second substrate 231 are stacked in this order, the first recessed part of the first substrate 221 has an opening portion facing the one surface of the membrane 210, the second recessed part of the second substrate 231 has an opening portion facing the other surface of the membrane 210, the one surface of the membrane 210 forms a part of the first flow path 220, the other surface of the membrane 210 forms a part of the second flow path 230, and the first flow path 220 and the second flow path 230 communicate with each other through the membrane 210; and a step of introducing a culture medium containing a lumenization factor into the first flow path 220.

In a case of seeding the bile duct epithelial cells 222 and culturing the cells in a culture medium containing a lumenization factor, a tube of the bile duct epithelial cells 222 is formed on the surface of the inner wall of the first flow path 220. The bile duct epithelial cells 222 may be primary cells, may be established cells, or may be cells obtained by being induced to differentiate from pluripotent stem cells. Examples of the pluripotent stem cell include an embryonic stem cell (ESC) and an induced pluripotent stem cell (iPSC).

As will be described later in Examples, examples of the lumenization factor include any one or more kinds of factors selected from the group consisting of Delta Like Canonical Notch Ligand 1 (DLL1) and Delta Like Canonical Notch Ligand 4 (DLL4).

In a case of adding a lumenization factor to a culture medium, the formation of a bile duct-like structure by the bile duct epithelial cells 222 is accelerated. It is more preferable that the lumenization factor is DLL1. The concentration of the lumenization factor in the culture medium is preferably about 1 to 100 ng/mL and more preferably about 10 ng/mL.

The producing method according to the present embodiment may further include a step of seeding the second cells 232 in the second flow path 230 after the bile duct epithelial cells 222 are disposed on a surface of an inner wall of the first flow path 220 to form a tube. As a result, the second cells 232 are adjacent to the bile duct epithelial cells 222 across the membrane 210.

The second cells 232 may include any one or more kinds of cells selected from the group consisting of liver cells and intestinal cells. The liver cells are the same as those described above. In a case where the second cells 232 are liver cells, the above-described tube serves as a model that mimics an intrahepatic bile duct in vivo.

[Method for Evaluating Bile Acid Kinetics]

In one embodiment, the present invention provides a method for evaluating bile acid kinetics, the method including a step of adding a test substance into a first flow path or a second flow path of a bile duct chip which includes a membrane through which substances are movable from one surface to the other surface, a first substrate having a first recessed part that forms a first flow path, and a second substrate having a second recessed part that forms a second flow path, where the first substrate, the membrane, and the second substrate are stacked in this order, the first recessed part of the first substrate has an opening portion facing the one surface of the membrane, the second recessed part of the second substrate has an opening portion facing the other surface of the membrane, the one surface of the membrane forms a part of the first flow path, the other surface of the membrane forms a part of the second flow path, the first flow path and the second flow path communicate with each other through the membrane, bile duct epithelial cells are disposed on a surface of an inner wall of the first flow path to form a tube, and liver cells are disposed in the second flow path; and a step of measuring an abundance of bile acid in the first flow path or the second flow path, or an expression level of a gene or a protein, which is associated with bile acid kinetics in the bile duct epithelial cells or the liver cells.

Bile acid kinetics can be evaluated according to the method according to the present embodiment. The method according to the present embodiment is a method of evaluating bile acid kinetics using an intrahepatic bile duct chip in which liver cells are disposed in the second flow path of the bile duct chip 200 described above.

In a description with reference to FIG. 2(*c*), the method according to the present embodiment is a method including a step of adding a test substance into the first flow path 220 or the second flow path 230 of a bile duct chip which includes a membrane 210 through which substances are movable from one surface to the other surface, a first substrate 221 having a first recessed part that forms a first flow path 220, and a second substrate 231 having a second recessed part that forms a second flow path 230, where the first substrate 221, the membrane 210, the second substrate 231 are stacked in this order, the first recessed part of the first substrate 221 has an opening portion facing the one surface of the membrane 210, the second recessed part of the second substrate 231 has an opening portion facing the other surface of the membrane 210, the one surface of the membrane 210 forms a part of the first flow path 220, the other surface of the membrane 210 forms a part of the second flow path 230, the first flow path 220 and the second flow path 230 communicate with each other through the membrane 210, the bile duct epithelial cells 222 are disposed on a surface of an inner wall of the first flow path 220 to form a tube, and the liver cells 232 are disposed in the second flow path 230; and a step of measuring an expression level of a gene or a protein, which is associated with an abundance of bile acid in the first flow path 220 or the second flow path 230, or bile acid kinetics in the bile duct epithelial cells 222 or the liver cells 232.

The test substance is not particularly limited, and examples thereof include a natural compound library, a synthetic compound library, an existing drug library, and a metabolite library.

Examples of the gene or protein associated with bile acid kinetics include a BSEP gene, an MRP2 gene, an NTCP gene, a CYP7A1 gene, and proteins encoded by these genes.

According to the method according to the present embodiment, it is also possible to evaluate the kinetics of another factor together with the kinetics of bile acid. Examples of the other factor include one or more kinds of factors selected from the group consisting of an in vivo compound other than bile acid, a drug, and a pathogen.

EXAMPLES

Next, the present invention will be described in more detail by showing Examples; however, the present invention is not limited to Examples below.

Material and Method

[Producing of Microfluidic Device]

As shown in FIG. 2(*a*) and FIG. 2(*b*), a microfluidic device was composed of two layers of flow paths separated by a semi-permeable membrane. The layer of the flow path was produced according to a soft lithography technique using polydimethylsiloxane (PDMS) as a material.

A PDMS prepolymer (Sylgard 184, Dow Corning Corp.) and a curing agent were mixed at a mixing ratio of PDMS prepolymer:curing agent=10:1, and the resultant mixture was cast into a mold formed on a silicon wafer, which had a pattern of SU-8 2150 (MicroChem corp.). The size of a cross section of the flow path had a width of 1 mm and the height of 300 μm. An access hole was drilled in the PDMS with a 6 mm biopsy punch (KAI CORPORATION) to introduce a liquid into the flow path.

The two PDMS layers were each adhered to a semi-permeable polyethylene terephthalate (PET) membrane (#353091 Falcon) having pores of 3 μm using a thin layer of a liquid PDMS prepolymer as a mortar.

The PDMS prepolymer was subjected to spin coating (4,000 rpm, 60 seconds) onto a glass slide. Subsequently, the upper layer and the lower layer were disposed on a slide glass, and a thin layer of the PDMS prepolymer was transferred to the surface of the PDMS which had been subjected to emboss processing. As a result, the PDMS thin layer as a mortar was disposed only on the upper surface of the flow path (recessed part). Subsequently, a semi-permeable membrane was adhered to each of the lower layer flow path and the upper layer flow path, and then the lower layer and the upper layer were stacked such that the semi-permeable membrane of the lower layer and the semi-permeable membrane of the upper layer faced each other to be in contact. The combined layers were allowed to stand at room temperature for one day to remove air bubbles and subsequently placed in an oven at 60° C. overnight to cure the PDMS adhesive agent. As a result, the lower layer and the upper layer were adhered with the two semi-permeable membranes being sandwiched therebetween, whereby a microfluidic device having flow paths separated by the semi-permeable membranes was obtained.

The microfluidic device was sterilized by being placed under ultraviolet (UV) light for 1 hour prior to cell culture.

[Culturing of Primary Human Hepatocytes and HuCCT1 Cells with Device]

HuCCT1 cells were suspended at 5×10$^5$ cells/mL in an RPMI containing 10% bovine fetal serum (FBS), 1×GlutaMAX, and penicillin/streptomycin. 10 μL of the cell suspension was introduced into the fibronectin-coated lower layer flow path of the microfluidic device. One hour after seeding the cells, 200 μL of a culture medium was added to the upper layer flow path and the lower layer flow path.

Four days after seeding the HuCCT1 cells, primary human hepatocytes (PHH, Xenotech) were seeded in the upper layer flow path. Cryopreserved human hepatocytes were used. A vial of PHH was rapidly thawed in a shaking water bath at 37° C. Subsequently, the contents of the vial were transferred into a pre-warmed Cryopreserved Hepatocyte Recovery Medium (Thermo Fisher Scientific, Inc.), and the suspension was centrifuged at 1,200 rpm for 5 minutes at room temperature. Subsequently, PHH was suspended at 5×10$^6$ cells/mL with HCM (Lonza K.K.) containing 10% bovine fetal serum (FBS). 10 μL of the cell suspension was introduced into the type I collagen-coated upper layer flow path of the microfluidic device. One hour after seeding the cells, 200 μL of a culture medium was added to each of the upper layer flow path and the lower layer flow path.

[Culturing of Primary Human Hepatocyte and HUVEC with Device]

Human umbilical vein endothelial cells (HUVEC) were suspended at 5×10$^6$ cells/mL in an EGM-2 Endothelial Cell Growth Medium-2 Bullet Kit (Lonza K.K.). 10 μL of the cell suspension was introduced into the fibronectin-coated lower layer flow path of the microfluidic device. One hour after seeding the cells, 200 μL of a culture medium was added to the upper layer flow path and the lower layer flow path.

Four days after seeding HUVEC, PHH was seeded in the upper layer flow path. Cryopreserved human hepatocytes were used. A vial of PHH was rapidly thawed in a shaking water bath at 37° C. Subsequently, the contents of the vial were transferred into a pre-warmed Cryopreserved Hepatocyte Recovery Medium (Thermo Fisher Scientific, Inc.), and the suspension was centrifuged at 1,200 rpm for 5 minutes at room temperature. Subsequently, PHH was suspended at 5×10$^6$ cells/mL with HCM (Lonza K.K.) containing 10% bovine fetal serum (FBS). 10 μL of the cell suspension was introduced into the type I collagen-coated upper layer flow path of the microfluidic device. One hour after seeding the cells, 200 μL of a culture medium was added to each of the upper layer flow path and the lower layer flow path.

[Quantitative PCR]

ISOGEN (NIPPON GENE CO., LTD.) was used to separate total RNA from the cells. A Superscript VILO cDNA synthesis kit (Thermo Fisher Scientific, Inc.) was used to synthesize cDNA from the separated total RNA.

Quantitative RT-PCR was carried out using SYBR Green PCR Master Mix (Thermo Fisher Scientific, Inc.) and StepOnePlus qPCR system (Thermo Fisher Scientific, Inc.).

For the relative quantification of target mRNA levels, a $2^{-\Delta\Delta CT}$ method was used. Quantitative values of target genes were standardized with the quantitative value of glyceraldehyde triphosphate dehydrogenase (GAPDH), which is a housekeeping gene. The base sequences of PCR primers are shown in Table 1 below.

TABLE 1

| Gene symbol | 5' to 3', forward (Seq ID No:)/ reverse (Seq ID No:) |
|---|---|
| ARG1 | GTGGAAACTTGCATGGACAAC (1)/ AATCCTGGCACATCGGGAATC (2) |
| ALB | GCACAGAATCCTTGGTGAACAG (3)/ ATGGAAGGTGAATGTTTTCAGCA (4) |
| AAT | ACTGTCAACTTCGGGGACAC (5)/ CATGCCTAAACGCTTCATCA (6) |
| CYP3A4 | AAGTCGCCTCGAAGATACACA (7)/ AAGGAGAGAACACTGCTCGTG (8) |
| CYP7A1 | GAGAAGGCAAACGGGTGAAC (9)/ GCACAACACCTTATGGTATGACA (10) |
| BSEP | TGATCCTGATCAAGGGAAGG (11)/ TGGTTCCTGGGAAACAATTC (12) |
| MRP2 | TGAGCAAGTTTGAAACGCACAT (13)/ AGCTCTTCTCCTGCCGTCTCT (14) |
| CYP2B6 | GTCCCAGGTGTACCGTGAAG (15)/ CCCTTTTGGGAAACCTTCTG (16) |
| NTCP | AGAAGGTGGAGCAGGTGGT (17)/ ATCTTGGTCTGTGGCTGCTC (18) |
| GAPDH | GGTGGTCTCCTCTGACTTCAACA (19)/ GTGGTCGTTGAGGGCAATG (20) |
| AQP1 | ATTAACCCTGCTCGGTCCTT (21)/ ACCCTGGAGTTGATGTCGTC (22) |
| KRT19 | CTCCCGCGACTACAGCCACT (23)/ TCAGCTCATCCAGCACCCTG (24) |
| CDH5 | TTGGAACCAGATGCACATTGAT (25)/ TCTTGCGACTCACGCTTGAC (26) |
| PECAM1 | AACAGTGTTGACATGAAGAGCC (27)/ TGTAAAACAGCACGTCATCCTT (28) |
| SELE | AGAGTGGAGCCTGGTCTTACA (29)/ CCTTTGCTGACAATAAGCACTGG (30) |
| ACTA2 | AAAAGACAGCTACGTGGGTGA (31)/ GCCATGTTCTATCGGGTACTTC (32) |
| COL1A1 | GAGGGCCAAGACGAAGACATC (33)/ CAGATCACGTCATCGCACAAC (34) |
| CYP1A2 | CAATCAGGTGGTGGTGTCAG (35)/ GCTCCTGGACTGTTTTCTGC (36) |
| TGFBR2 | GGGGAAACAATACTGGCTGA (37)/ GAGCTCTTGAGGTCCCTGTG (38) |
| TIMP1 | CTTCTGCAATTCCGACCTCGT (39)/ ACGCTGGTATAAGGTGGTCTG (40) |

[Evaluation of Bild Acid Signaling]

PHH was treated with 100 μM chenodeoxycholic acid (CDCA, Sigma-Aldrich Co., LLC) or 2.5 μM GW4046 (CELLEC) for 72 hours. Subsequently, the expression levels of the BSEP gene and the CYP7A1 gene were measured according to quantitative PCT. The measurement value of the target gene was standardized with the measurement value of the GAPDH gene.

[Evaluation of Albumin (ALB) Secretion]

A culture supernatant was recovered to evaluate the ability of human ALB secretion by PHH. The recovered culture supernatant was analyzed using a Human Albumin ELISA Quantitation Set (Bethyl Laboratories, Inc.). Enzyme immunoassay (ELISA) was carried out according to the user's instruction manual.

[Evaluation of Bile Acid Secretion]

A culture supernatant was recovered to evaluate the ability of bile acid secretion. The recovered culture supernatant was analyzed using a total bile acid-test (FUJIFILM Wako Pure Chemical Corporation) according to the user's instruction manual.

[Bile Transport Assay]

0.05% bovine-derived bile (FUJIFILM Wako Pure Chemical Corporation) was added to the upper layer flow path of the microfluidic device. 48 hours after the bile was added, a culture supernatant from the lower layer flow path was recovered. The recovered culture supernatant was analyzed using a total bile acid-test (FUJIFILM Wako Pure Chemical Corporation) according to the user's instruction manual.

[CDFDA Transport Assay]

10 μM of 5(6)-carboxy-2',7'-dichlorofluorescein diacetate (CDFDA) was added to the upper layer flow path. After 3 hours, the culture supernatant from the lower layer flow path was recovered. The fluorescence intensity of 5(6)-carboxy-2',7'-dichlorofluorescein (CDF) in the recovered culture supernatant, which is a metabolite of CDFDA, was measured.

[Immunochemical Staining]

PHH was fixed for 15 minutes with 4% paraformaldehyde in phosphate buffered saline (PBS). The cells were blocked with PBS containing 10% FBS, 1% bovine serum albumin, and 0.2% Triton X-100 for 45 minutes at room temperature and subsequently incubated with a primary antibody overnight at 4° C., followed by incubation with a secondary antibody at room temperature for 1 hour. The antibodies used are shown in Table 2 below.

[Culturing of Primary Human Hepatocyte in Polystyrene Plate]

In the culturing of primary human hepatocytes on a polystyrene plate, the same operation as in the culturing with the device was carried out up to the centrifugation of PHH. Subsequently, the PHH suspended in HCM (Lonza K.K.) containing 10% FBS was seeded to $1\times10^5$ cells/cm 2 in a type I collagen-coated 96-well plate. The PHH 24 hours after seeding was used in the experiment.

[Examination of Acetaminophen-Induced Cytotoxicity]

PHH was exposed to 10 mM APAP (FUJIFILM Wako Pure Chemical Corporation) for 4 days. Cell viability was measured according to a WST-8 assay. The WST-8 assay was carried out using a Cell Counting Kit-8 (Dojindo Molecular Technologies. Inc.) according to the instruction manual. The cell viability was calculated as a percentage with respect to cells not subjected to a drug treatment.

[Measurement of CYP Activity Using Five Kinds of CYP Substrates]

The LC-MS/MS analysis was carried out to measure the activity of CYP. Prior to a CYP substrate treatment, PHH was cultured in DMEM containing 10 mM HEPES for 30 minutes. Subsequently, the PHH was cultured in a culture medium containing 5 μM MDZ (the metabolite thereof is 1OH-MDZ), 50 μM MPHT (the metabolite thereof is 4OH-MPHT), 5 μM DIC (the metabolite thereof is 4OH-DIC), 10 μM BUF (the metabolite thereof is 1OH-BUF), or 50 μM PHE (the metabolite thereof is APAP). The supernatant was recovered 1, 2, and 4 hours after the treatment with the substrate. At the time of recovering the supernatant, an equal amount of a culture medium containing the substrate was added.

TABLE 2

| Antibody | Selling company | Catalogue number |
|---|---|---|
| Anti-ALB antibody | Bethyl Laboratories, Inc. | A80-229A |
| Anti-BSEP antibody | Santa Cruz Biotechnology, Inc. | sc-74500 |
| Anti-KRT19 antibody | abcam. plc | ab52625 |
| Anti-CK8/18 antibody | Santa Cruz Biotechnology, Inc. | sc-52325 |
| Anti-HNF4A antibody | Santa Cruz Biotechnology, Inc. | sc-374229 |
| Donkey anti-Goat IgG (H + L) Highly Cross-Adsorbed Secondary Antibody, Alexa Fluor 488 | Thermo Fisher Scientific, Inc. | A-11055 |
| Donkey anti-Goat IgG (H + L) Highly Cross-Adsorbed Secondary Antibody, Alexa Fluor 594 | Thermo Fisher Scientific, Inc. | A-11058 |
| Donkey anti-Mouse IgG (H + L) Highly Cross- Adsorbed Secondary Antibody, Alexa Fluor 488 | Thermo Fisher Scientific, Inc. | A-21202 |
| Donkey anti-Mouse IgG (H + L) Highly Cross- Adsorbed Secondary Antibody, Alexa Fluor 594 | Thermo Fisher Scientific, Inc. | A-21203 |
| Goat anti-rabbit IgG (H + L) Highly Cross-Adsorbed Secondary Antibody, Alexa Fluor 594 | Thermo Fisher Scientific, Inc. | A-11012 |

[GFP-Expressing HuCCT1 Cell]

Using Lipofectamine 2000 (Thermo Fisher Scientific, Inc.), pPV-EF1a-EiP-A, which is an EGFP expression vector based on a PiggyBac vector, was transfected into HuCCT1 cells together with pHL-EF1a-hcPBase-A, which is a PiggyBac transposase vector, and selection was carried out with puromycin. All of the above vectors were obtained from Dr. Akitsu Hotta (the Center for iPS Cell Research and Application, Kyoto University).

The recovered supernatant was mixed with acetonitrile (FUJIFILM Wako Pure Chemical Corporation) containing an equal volume of 5 μM propranolol (internal standard). The specimen was filtered through a Cosmonice Filter W (Nacalai Tesque, Inc.) having a pore size of 0.45 μm, the supernatant was subsequently analyzed by LC-MS/MS, and the concentration of the metabolite was measured based on the standard curve. The LC-MS/MS analysis was carried out using LCMS-8040 (Shimadzu Corporation).

Table 3 below shows the ionization mode and multiple-reaction monitoring (MRM) transition of the mass spectrometer. The retention time of each MRM transition was set to 100 milliseconds.

TABLE 3

| | Selling company | Ionization mode | MRM transition | Collision energy |
|---|---|---|---|---|
| midazolam | FUJIFILM Wako Pure Chemical Corporation | positive | 326.80/ 292.10 | −27 V |
| S-mephenytoin | Toronto Research Chemicals | negative | 217.30/ 188.15 | 18 V |
| diclofenac | Tokyo Chemical Industry Co., Ltd. | negative | 295.10/ 251.10 | 11 V |
| bufuralol | Toronto Research Chemicals | positive | 262.25/ 188.10 | −16 V |
| phenacetin | Nacalai Tesque, Inc. | positive | 180.15/ 110.10 | −23 V |
| 1'-hydroxymidazolam | Cayman Chemical Company | positive | 342.80/ 325.10 | −23 V |
| 4'-hydroxymephenytoin | Toronto Research Chemicals | negative | 233.10/ 190.15 | 14 V |
| 4'-hydroxydiclofenac | Cayman Chemical Company | positive | 313.10/ 231.00 | −33 V |
| 1'-hydroxybufuralol | Toronto Research Chemicals | positive | 270.05/ 186.10 | −19 V |
| acetaminophen | Nacalai Tesque, Inc. | positive | 151.95/ 110.00 | −18 V |
| Propranolol (IS) | Nacalai Tesque, Inc. | positive | 260.35/ 116.15 | −17 V |

The LC separation was carried out at 40° C. using an XBride BEH C18 column 1.7 μm, 2.1×50 mm (Waters Corporation). The conditions of the mobile phase are shown in Table 4 below.

TABLE 4

| Items other than MPHT, 4OH-MPHT | | |
|---|---|---|
| solvent A | 0.1% formic acid | |
| solvent B | 0.1% formic acid-acetonitrile | |
| T. flow: | 0.2 mL/minute | |
| B. conc: | 10% | 0 to 1 minutes |
| | 10→30% | 1 to 1.5 minutes |
| | 30% | 1.5 to 2.5 minutes |
| | 30→95% | 2.5 to 3 minutes |
| | 95% | 3 to 4 minutes |
| | 95→10% | 4 to 4.5 minutes |
| | 10% | 4.5 to 5.5 minutes |
| sample injection | 1 or 5 μL | |
| **MPHT and 4OH-MPHT** | | |
| solvent A | 10 mM ammonium acetate | |
| solvent B | acetonitrile | |
| T. flow: | 0.3 mL/minute | |
| B. conc: | 10% | 0 to 1 minutes |
| | 10→90% | 1 to 3 minutes |
| | 90% | 3 to 4 minutes |
| | 90→10% | 4 to 4.5 minutes |
| | 10% | 4.5 to 6 minutes |
| sample injection | 5 μL | |

[Measurement of Atorvastatin Metabolism by CYP3A]

The formation of 20H-ATV was observed in order to examine the metabolism of atorvastatin (ATV), which is a substrate of both ATP1Bs and CYP3A in the liver.

Prior to adding the substrate, PHH was cultured for 30 minutes in DMEM containing dimethyl sulfoxide (DMSO) or 100 μM SKF-525A (Toronto Research Chemicals), and 10 mM HEPES. Subsequently, the PHH was cultured in a culture medium containing 1 μM ATV (FUJIFILM Wako Pure Chemical Corporation). The supernatant was recovered 1, 2, and 4 hours after the treatment with the substrate. At the time of recovering the supernatant, an equal volume of a culture medium containing the substrate was added.

A fraction (20 μL) of the recovered supernatant was mixed with 20 μL of Milli-Q water and 120 μL of acetonitrile containing 120 μL of 10 nM of an internal standard (fluvastatin, FUJIFILM Wako Pure Chemical Corporation). After centrifugation, 100 μL of the supernatant was analyzed by LC-MS/MS. In a case where an analysis product had a high concentration, the supernatant was diluted 40 folds with Milli-Q water as necessary.

Chromatography was carried out using a Nexera X2 LC system (Shimadzu Corporation), and quantification was carried out using QTRAP 5500+ (AB Sciex LLC).

A standard substance for 2OH-ATV was purchased from Toronto Research Chemicals.

A mass spectrometer was set to an MRM mode and operated with an electrospray ionization source. The ATV quantification was carried out in a positive ion mode, and the quantification of 20H-ATV and fluvastatin was carried out in a negative ion mode.

The MRM transition (in terms of a ratio of m/z of precursor ion to m/z of product ion) was 559.1/440.2 (ATV), 573.1/278.1 (2OH-ATV), or 410.0/348.0 (fluvastatin). For the transition, the collision energy was set to 31 V (ATV), −52 V (2OH-ATV), or −22 V (fluvastatin).

The LC separation was carried out at 40° C. using a PC HILIC (2.0 mm i.d.×150 mm, 3 μm, OSAKA SODA CO., LTD.). A mixture of a 30% solvent A (0.1% formic acid in 10 mM ammonium acetate/20% acetonitrile) and a 70% solvent B (0.1% formic acid in 10 mM ammonium acetate/95% acetonitrile) was used as a mobile phase, and liquid feeding was carried out at a flow rate of 0.4 mL/min. The acquisition and treatment of data were carried out using Analyst (R) software version 1.7.1 (AB Sciex LLC)).

[CYP Induction Test]

PHH was treated with 50 μM omeprazole, 500 μM phenobarbital, or 20 μM rifampicin (all of which are from FUJIFILM Wako Pure Chemical Corporation) for 48 hours. Each of these drugs is known to induce CYP1A2, 2B6, and 3A4.

In order to measure the inducibility of CYP1A2, 2B6, and 3A4, the expression level of CYP was measured by quantitative RT-PCR. The expression level of the target gene was standardized with the expression level of GAPDH. The inducibility was calculated as a change in expression level in terms of folds in cells treated with DMSO. The PCR primer sequences are shown in Table 1 above.

[Measurement of Active TGF-β1]

PHH was treated with 100 ng/mL of TGF-β1 for 48 hours. In order to quantify active TGF-β1 in the supernatant, the culture medium was recovered and analyzed according to the instruction manual using a TGF beta-1 Human ELISA Kit (BMS249-4, Thermo Fisher Scientific, Inc.). The amount of active TGF-β1 was calculated based on each standard.

[Statistical Analysis]

Statistical analysis was evaluated according to the unpaired two-sided Student's t test. Statistical significance was evaluated according to the one-way analysis of variance (ANOVA) and the subsequent Dunnett's test or Tukey's test. The details thereof will be described later.

Experimental Example 1

[Preparation of Intrahepatic Bile Duct Chip (Intrahepatic Bile Duct-On-a-Chip) Using Primary Human Hepatocytes and HuCCT1 Cell]

FIG. 1 is a schematic view showing a structure of an intrahepatic bile duct in vivo. FIG. 2 is a schematic view of an intrahepatic bile duct chip (intrahepatic bile duct-on-a-chip, IHBD chip). The intrahepatic bile duct chip 200 is composed of two flow paths and the PET membrane 210. The upper layer flow path 230 and the lower layer flow path 220 are divided by the membrane 210.

The primary human hepatocytes (PHH) 232 were seeded in the inside of the upper layer flow path 230 of the intrahepatic bile duct chip 200, and the HuCCT1 cells 222, which are a human bile duct cancer cell line, were seeded in the inside of the lower layer flow path 220 of the device 200. As a result of culturing the HuCCT1 cells 222 in the inside of the lower layer flow path 220, the HuCCT1 cells formed a tubular structure.

Figure 3:
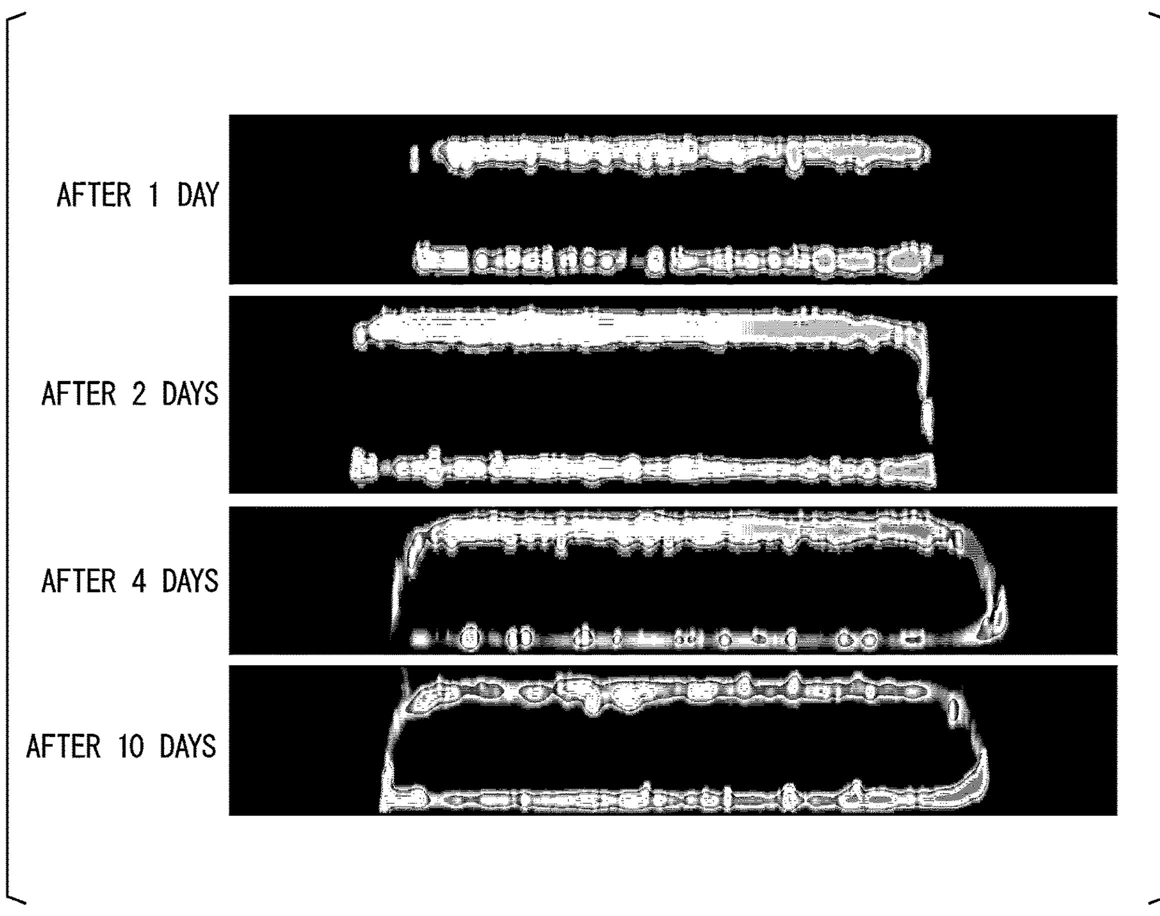
FIG. 3 shows fluorescence microscopic images of cross sections, which have captured 1, 2, 4, and 10 days after culturing GFP-expressing HuCCT1 cells in the inside of a flow path of a microfluidic device in Experimental Example 1.

FIG. 3 shows fluorescence microscopic images of cross sections, which have captured 1, 2, 4, and 10 days after culturing GFP-expressing HuCCT1 cells in the inside of the lower layer flow path 220. As shown in FIG. 3, the GFP-expressing HuCCT1 cells formed a tubular structure.

Figure 4:
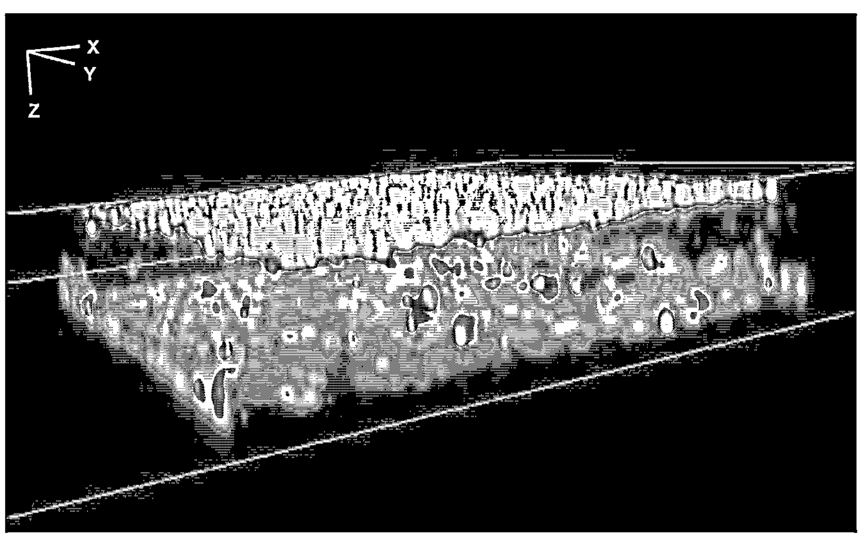
FIG. 4 is an image showing results of analyzing an intrahepatic bile duct chip according to immunochemical staining in Experimental Example 1.
Figure 5:
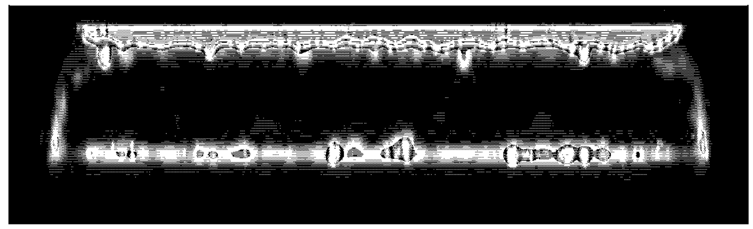
FIG. 5 is an image showing results of analyzing an intrahepatic bile duct chip according to immunochemical staining in Experimental Example 1.
Figure 6:
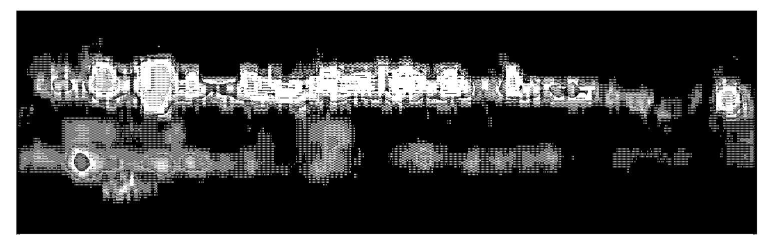
FIG. 6 is an image showing results of analyzing an intrahepatic bile duct chip according to immunochemical staining in Experimental Example 1.

FIGS. 4 to 6 are images showing results of analyzing an intrahepatic bile duct chip according to immunochemical staining. HuCCT1 cells were seeded in the lower layer flow path, and after 4 days, PHH was seeded in the upper layer flow path. Subsequently, immunostaining of ALB and CK19 was carried out. In addition, the nuclei were stained with DAPI.

FIG. 4 shows a confocal image, and FIG. 5 shows a cross section of the intrahepatic bile duct chip. As a result, it was revealed that CK19-positive HuCCT1 cells have formed a cyclic structure in the device. FIG. 6 is an enlarged image of the periphery of the membrane of the intrahepatic bile duct chip. FIG. 6 shows that a monolayer of ALB-positive hepatocytes is adjacent to a bile duct-like structure.

From the above results, it was shown that the inventors of the present invention have succeeded in producing an intrahepatic bile duct chip having a monolayer of hepatocytes and a tubular bile duct-like structure.

Experimental Example 2

[Examination of Hepatic Function of Hepatocyte Cultured with Intrahepatic Bile Duct Chip]

It was examined whether or not the hepatic function of PHH was changed by co-culturing with HuCCT1 cells using a microfluidic device.

Figure 7:
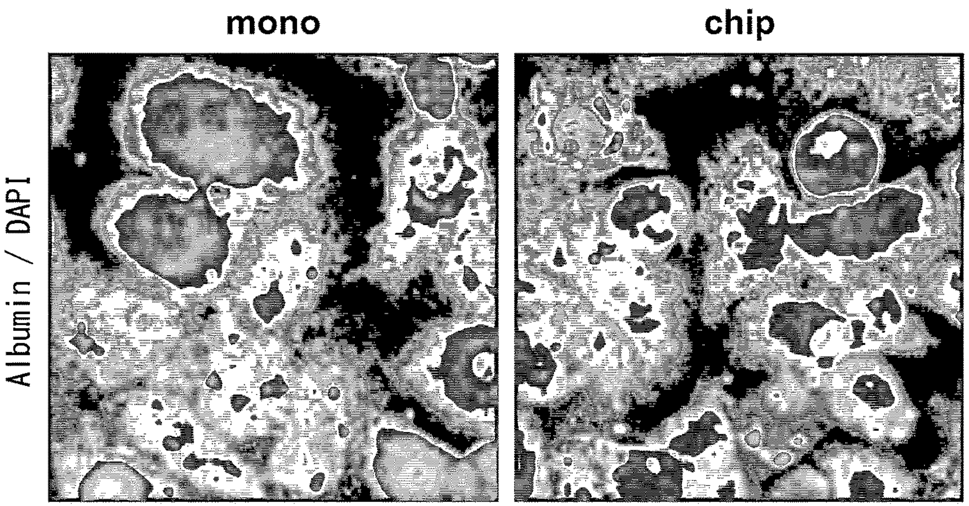
FIG. 7 shows fluorescence microscopic images showing results of immunostaining of primary human hepatocytes (PHH) co-cultured with HuCCT1 cells with an intrahepatic bile duct chip in Experimental Example 2.

FIG. 7 shows fluorescence microscopic images showing results of immunostaining of the PHH co-cultured with HuCCT1 cells with intrahepatic bile duct chip (indicated as "chip" in FIG. 7). First, HuCCT1 cells were seeded in the lower layer flow path of the microfluidic device. Four days after seeding the HuCCT1 cells, PHH was seeded in the upper layer flow path of the same microfluidic device. Subsequently, ALB in the PHH cultured with the intrahepatic bile duct chip was immunostained. In addition, the nuclei were stained with DAPI.

In addition, for comparison, immunostaining was also carried out in a case where only PHH was cultured without seeding HuCCT1 cells in a microfluidic device (indicated as "mono" in FIG. 7).

As a result, it was shown that the expression level of ALB in the PHH cultured with the intrahepatic bile duct chip is similar to the expression level of ALB in the PHH-only chip (mono).

Subsequently, the gene expression levels of liver markers (ARG1, ALB, AAT, CYP3A4, and CYP2B6) and bile acid-related genes (BSEP, MRP2, and CYP7A1) were measured by quantitative RT-PCR.

Figure 8:
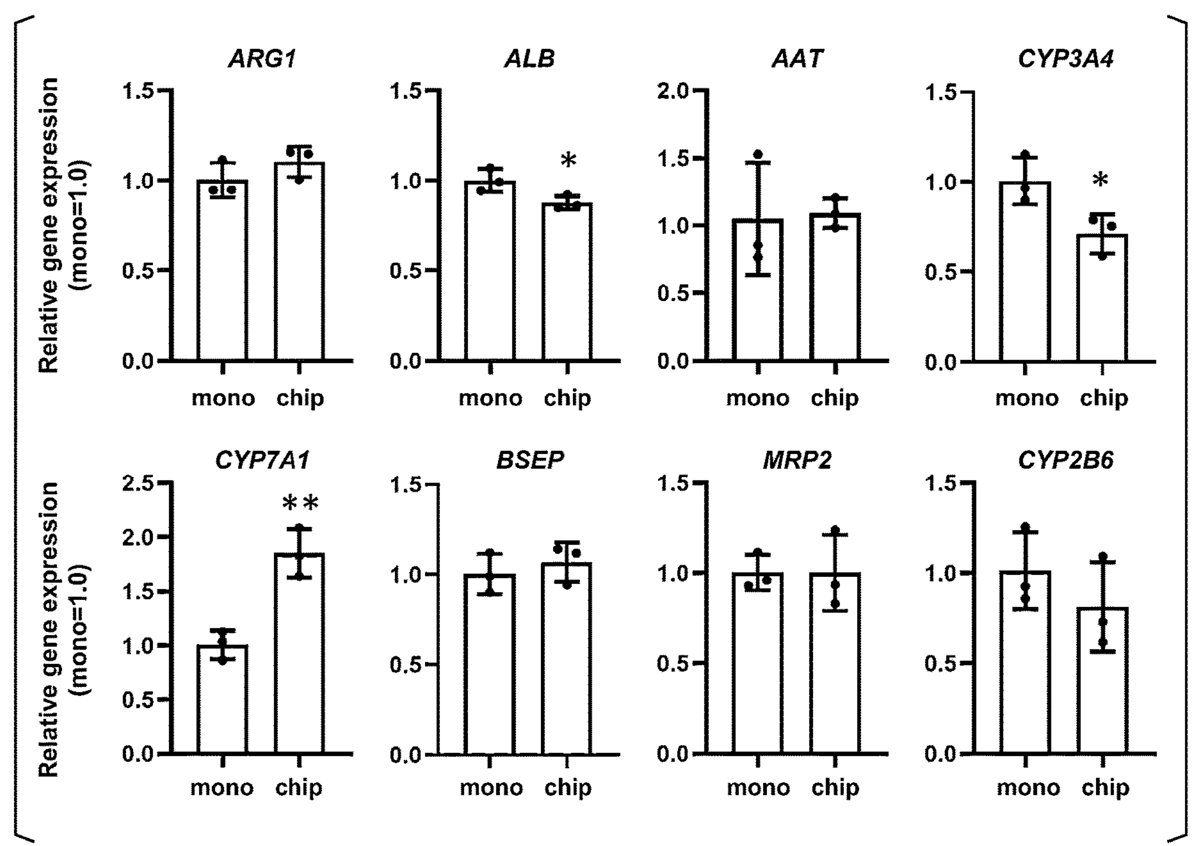
FIG. 8 shows graphs showing results of quantitative RT-PCR in Experimental Example 2.

FIG. 8 shows graphs showing results of quantitative RT-PCR. In FIG. 8, "mono" indicates that the results are for a case where only PHH is cultured without seeding HuCCT1 cells in the microfluidic device. In addition, "chip" indicates that the results are for a case where HuCCT1 cells and PHH have been co-cultured for 7 days in the microfluidic device. The vertical axis indicates a relative value of the expression level of each gene in a case where the expression level in the case of "mono" is set to 1. In addition, "*" indicates that there is a significant difference at $p<0.05$, and "**" indicates that there is a significant difference at $p<0.01$. All data are indicated as average value±standard deviation (n=3).

As a result, in the intrahepatic bile duct chip (chip), the gene expression levels of a part of the liver markers such as ALB and CYP3A4 were slightly decreased; however, the expression levels of most of the genes were not affected by the co-culturing in the intrahepatic bile duct chip.

In addition, the response to bile acid signaling in PHH was examined. Chenodeoxycholic acid (CDCA) is one of the major bile acids. The PHH and the HuCCT1 cells of the intrahepatic bile duct chip were treated with 100 μM CDCA for 72 hours.

In addition, a specimen treated with dimethyl sulfoxide (DMSO) instead of CDCA was also prepared for comparison. Subsequently, the gene expression levels of BSEP, NTCP, and CYP7A1 were measured according to quantitative RT-PCR.

Figure 9:
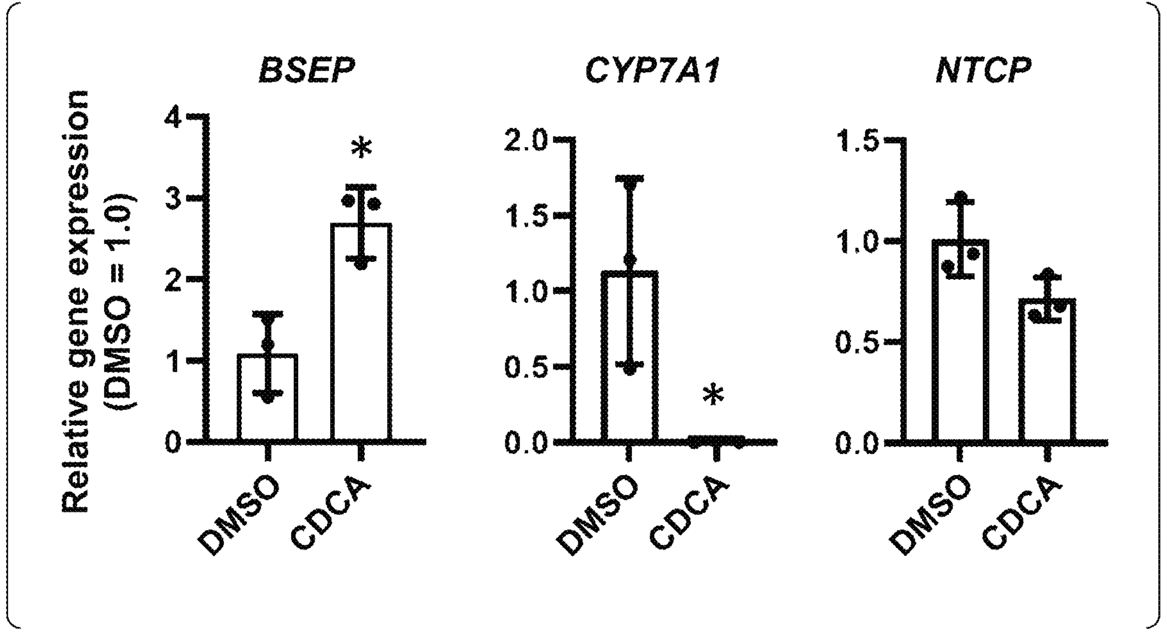
FIG. 9 shows graphs showing results of quantitative RT-PCR in Experimental Example 2.

FIG. 9 shows graphs showing results of quantitative RT-PCR. In FIG. 9, the vertical axis indicates a relative value of the expression level of each gene in a case where the expression level in a case where DMSO has been treated is set to 1. In addition, "*" indicates that there is a significant difference at $p<0.05$. All data are indicated as average value±standard deviation (n=3).

As a result, it was shown that in a case where CDCA is treated, the gene expression levels of the bile acid transporters (BSEP and NTCP) in the intrahepatic bile duct chip are increased, and the gene expression level of the bile acid synthase (CYP7A1) is decreased. This result indicates that the PHH cultured with the intrahepatic bile duct chip has the hepatic function.

Experimental Example 3

[Reproduction of Bile Acid Kinetics Using Intrahepatic Bile Duct Chip]

The flow of bile acid was examined using the intrahepatic bile duct chip. For comparison, a model (blood vessel chip) in which PHH and human umbilical vein endothelial cells (HUVEC) were co-cultured with the microfluidic device was also produced. Specifically, HuCCT1 cells or HUVEC were seeded in the lower layer flow path of the microfluidic device. Subsequently, 4 days after seeding of the cells, PHH was seeded in the upper layer flow path of the microfluidic device.

Figure 10:
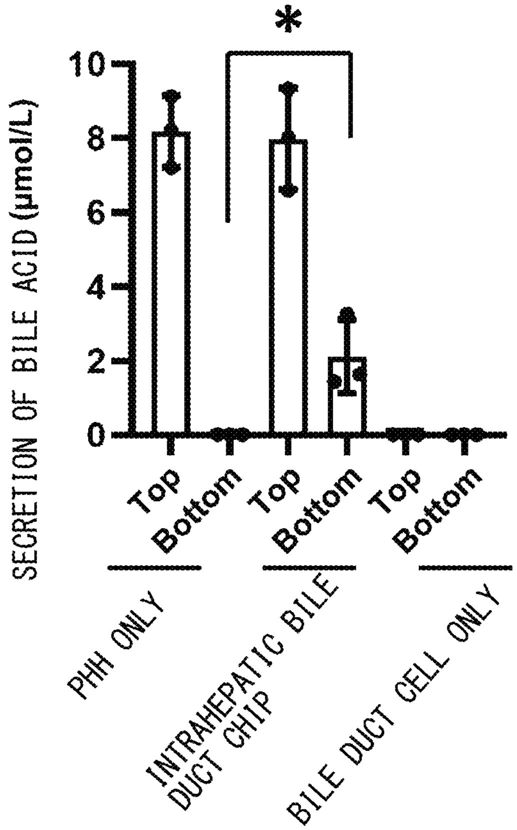
FIG. 10 is a graph showing results of quantifying bile acid in Experimental Example 3.

First, the amount of bile acid secreted into the culture medium from the PHH was measured. FIG. 10 is a graph showing results of quantifying bile acid. In FIG. 10, "PHH only" indicates that the results are for a case where only PHH is cultured without seeding HuCCT1 cells in the microfluidic device. In addition, "bile duct cell only" indicates the results for a case where only HuCCT1 cells are cultured with the microfluidic device and PHH is not seeded. In addition, "intrahepatic bile duct chip" indicates that the results are for a case where HuCCT1 cells and PHH have been co-cultured in the microfluidic device. In FIG. 10, "*" indicates that there is a significant difference at $p<0.05$.

As a result, it was revealed that bile acid is directionally transported to the lower layer flow path of the intrahepatic bile duct chip.

Figure 11:
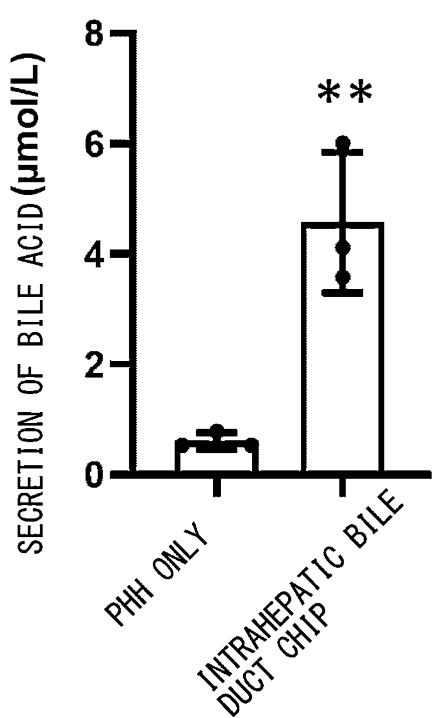
FIG. 11 is a graph showing results of quantifying bile acid in Experimental Example 3.

Subsequently, bovine-derived bile was added to the upper layer flow path of the intrahepatic bile duct chip, and after 48 hours, the culture medium was recovered from the lower layer flow path, and the bile acid in the culture medium was quantified. FIG. 11 is a graph showing results of quantifying bile acid. In FIG. 11, "PHH only" indicates that the results are for a case where only PHH is cultured without seeding HuCCT1 cells in the microfluidic device. In addition, "intrahepatic bile duct chip" indicates that the results are for a case where HuCCT1 cells and PHH have been co-cultured in the microfluidic device. In FIG. 11, "**" indicates that there is a significant difference at $p<0.01$.

As a result, it was revealed that the co-culturing with HuCCT1 cells increases the amount of the bile acid transported to the lower layer flow path of the intrahepatic bile duct chip.

Bile acid is known to be excreted into the bile canaliculus via BSEP, which is a hepatic transporter. The localization of BSEP was checked by immunostaining in order to examine the reason why bile acid was directionally transported to the lower layer flow path.

Figure 12:
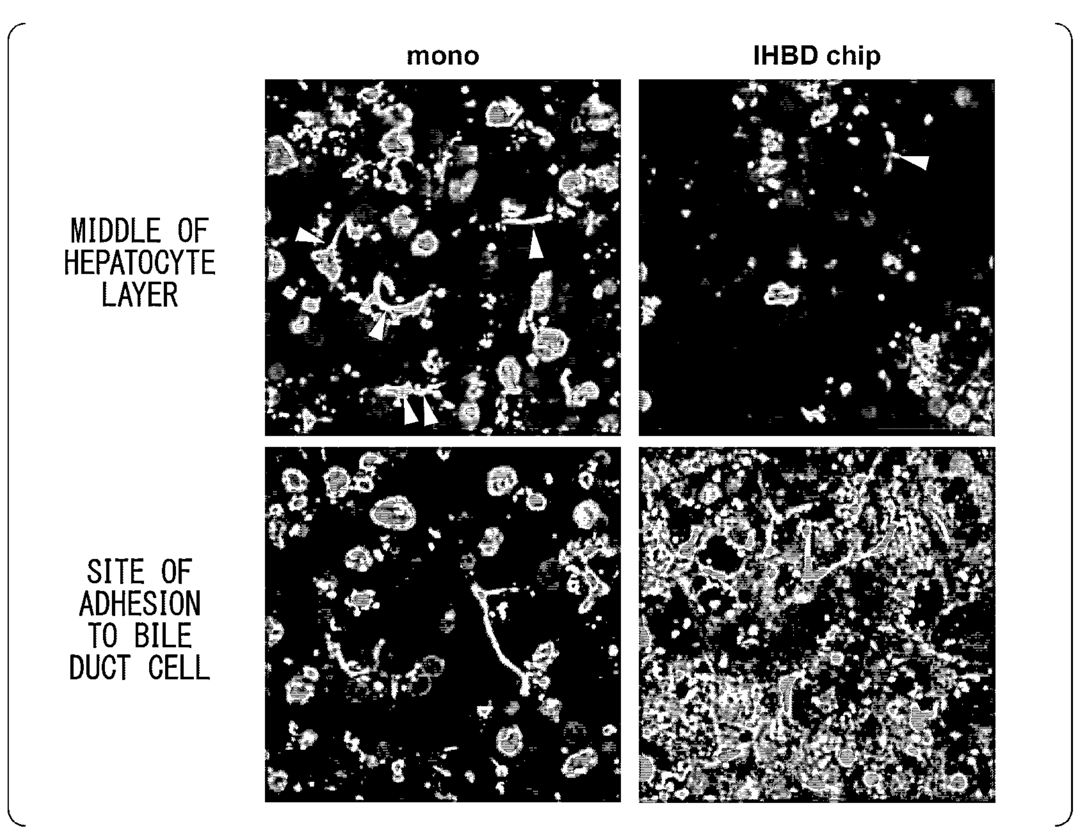
FIG. 12 shows fluorescence microscopic images in which BSEP, which is a bile acid transporter, has been stained by immunostaining of the PHH cultured with an intrahepatic bile duct chip in Experimental Example 3.

FIG. 12 shows fluorescence microscopic images in which BSEP, which is a bile acid transporter, has been stained by immunostaining of the PHH cultured with an intrahepatic bile duct chip. The nuclei were stained with DAPI. In FIG. 12, "mono" indicates that the results are for a case where only PHH is cultured without seeding HuCCT1 cells in the microfluidic device, and "IHBD chip" indicates that the results are for a case where HuCCT1 cells and PHH have been co-cultured for 7 days in the microfluidic device. In FIG. 12, arrowheads indicate the localization of BSEP.

As a result, the expression level of BSEP in the middle of the hepatocyte layer was high in the PHH-only chip as compared with the intrahepatic bile duct chip. However, at the site of adhesion to HuCCT1 cells, the expression level of BSEP was high in the intrahepatic bile duct chip as compared with the PHH-only chip. This result suggests that the localization of BSEP contributes to the directional transport of bile acid to the lower layer flow path.

Subsequently, 5(6)-carboxy-2',7'-dichlorofluorescein diacetate (CDFDA) was added to the upper layer flow path of the intrahepatic bile duct chip, and after 3 hours, the fluorescence of the culture medium in the lower layer flow path was measured. In living cells, CDFDA is hydrolyzed to 5(6)-carboxy-2',7'-dichlorofluorescein (CDF). CDF is a substrate of MRP2, which is a transporter. Therefore, the CDF transported to the lower layer flow path can be quantified by measuring the fluorescence intensity.

Figure 13:
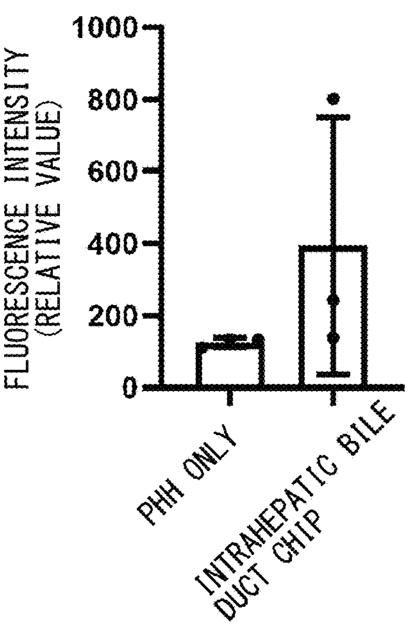
FIG. 13 is a graph showing results of measuring the fluorescence intensity of 5(6)-carboxy-2',7'-dichlorofluorescein (CDF) in Experimental Example 3.

FIG. 13 is a graph showing results of measuring the fluorescence intensity. In FIG. 13, "PHH only" indicates that the results are for a case where only PHH is cultured without seeding HuCCT1 cells in the microfluidic device. In addition, "intrahepatic bile duct chip" indicates that the results are for a case where HuCCT1 cells and PHH have been co-cultured in the microfluidic device. In FIG. 13, "*" indicates that there is a significant difference at $p<0.05$.

As a result, it was revealed that the co-culturing with HuCCT1 cells increases the amount of the CDF transported to the lower layer flow path of the intrahepatic bile duct chip.

Subsequently, the albumin in the culture medium was quantified. In vivo, albumin is produced in hepatocytes and secreted into the blood plasma. GFP-expressing HuCCT1 cells or GFP-expressing HUVEC was seeded in the lower layer flow path, and after 4 days, PHH was seeded in the upper layer flow path. Subsequently, after one day, the secretion of albumin in the intrahepatic bile duct chip or blood vessel chip was measured according to ELISA.

Figure 14:
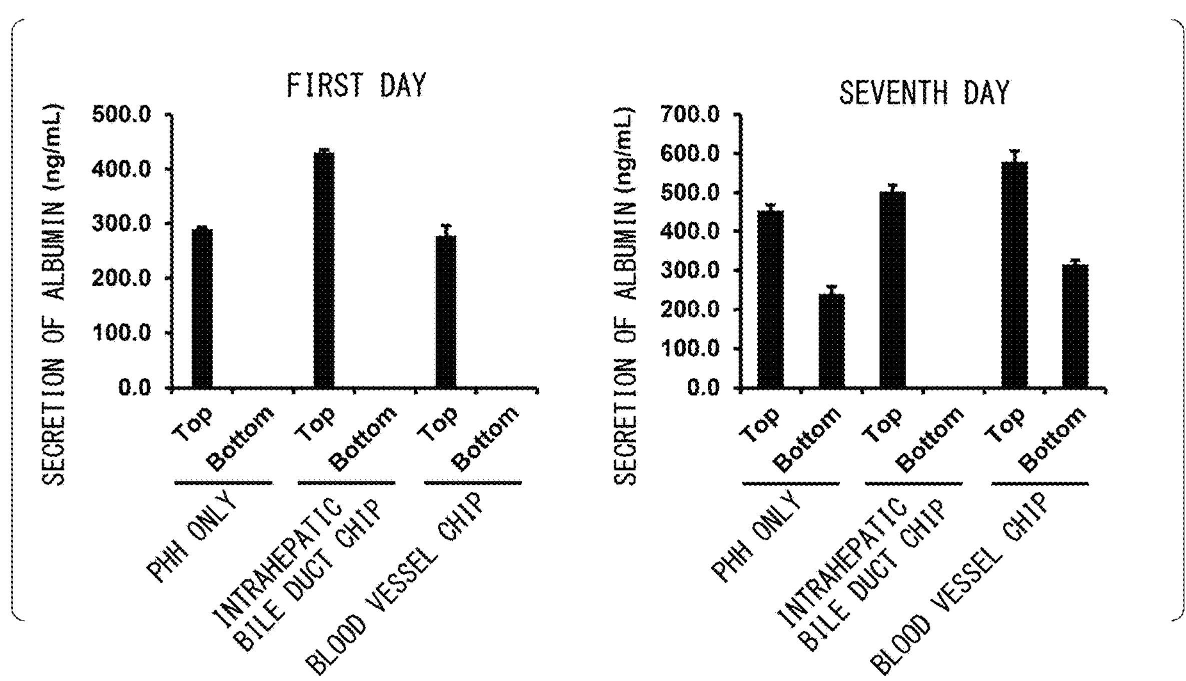
FIG. 14 shows graphs showing results of quantifying albumin in an upper layer flow path and a lower layer flow path according to ELISA in Experimental Example 3.

FIG. 14 shows graphs showing results of quantifying albumin in an upper layer flow path (Top) and a lower layer flow path (Bottom) according to ELISA after 1 day or 7 days from the start of co-culturing.

As a result, after 7 days from the start of co-culturing, albumin was directionally transported to the lower layer flow path of the blood vessel chip. However, albumin was not transported to the lower layer flow path of the intrahepatic bile duct chip.

The above results indicate that it is possible to reproduce the kinetics of bile acid by using the intrahepatic bile duct chip.

Experimental Example 4

[Production of Intrahepatic Bile Duct Chip Using Human iPS Cell]

An intrahepatic bile duct chip containing hepatocyte-like cells derived from human iPS cells was produced. GFP-expressing HuCCT1 cells were seeded in the lower layer flow path, and after 4 days, hepatocyte-like cells derived from human iPS cells were seeded in the upper layer flow path. Subsequently, the expression of cytokeratin 18 (CK18) in the intrahepatic bile duct chip, which is a liver marker, was analyzed according to immunochemical staining.

Figure 15:
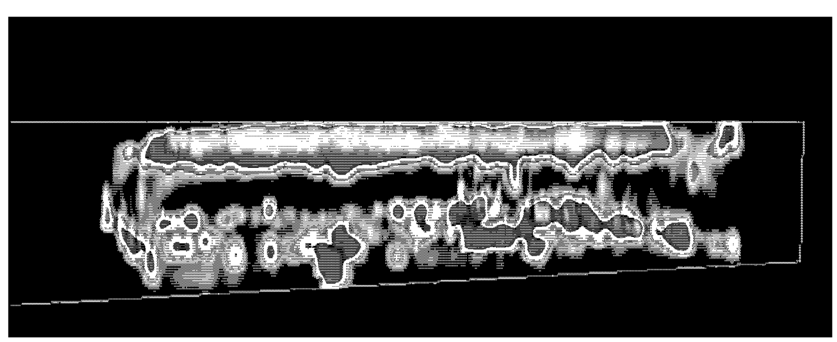
FIG. 15 is a confocal image of an intrahepatic bile duct chip in Experimental Example 4.
Figure 16:
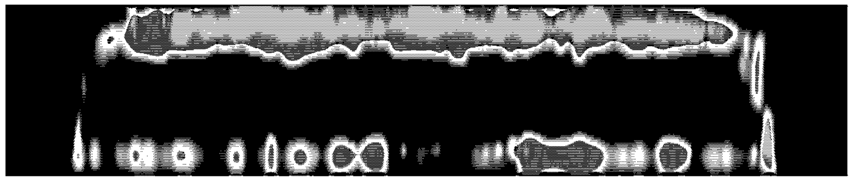
FIG. 16 is an image showing a cross section of an intrahepatic bile duct chip in Experimental Example 4.

FIG. 15 is a confocal image, and FIG. 16 is an image showing a cross section of the intrahepatic bile duct chip. As a result, similar to the case of culturing the primary hepatocytes, it was shown that the iPS cell-derived hepatocyte-like cells can form a monolayer and connect to a tubular bile duct-like structure.

Subsequently, using an intrahepatic bile duct chip containing hepatocyte-like cells derived from human iPS cells, the bile acid secreted into the culture medium of the upper layer flow path (Top) and the lower layer flow path (Bottom) was measured.

Figure 17:
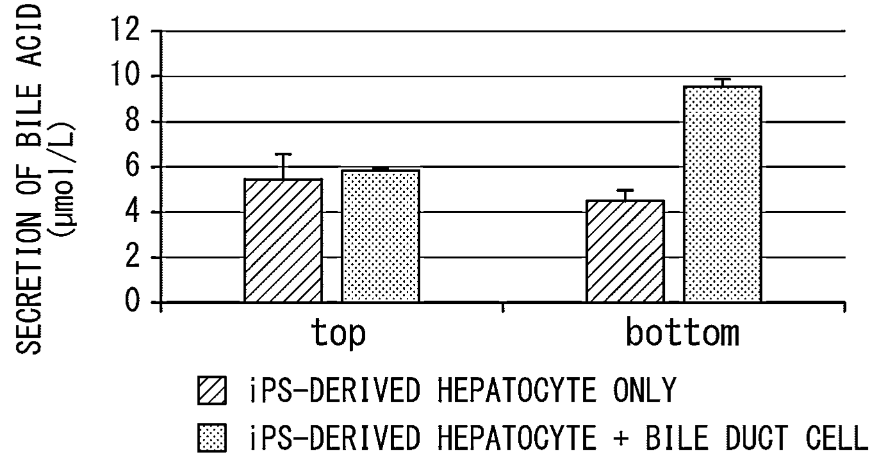
FIG. 17 is a graph showing results of quantifying bile acid in Experimental Example 4.

FIG. 17 is a graph showing results of quantifying bile acid. As a result, it was confirmed that the bile acid kinetics can be reproduced by the intrahepatic bile duct chip containing hepatocyte-like cells derived from human iPS cells.

Experimental Example 5

[a Treatment with Recombinant Human DLL1 or DLL4 Accelerated the Formation of a Tubular Bile Duct-Like Structure in the Intrahepatic Bile Duct Chip.]

GFP-expressing HuCCT1 cells were seeded in the lower layer flow path of the microfluidic device in the presence or absence of 10 ng/mL of DLL1 or DLL4, and after 4 days, a cross-sectional image of the microfluidic device was acquired.

Figure 18:
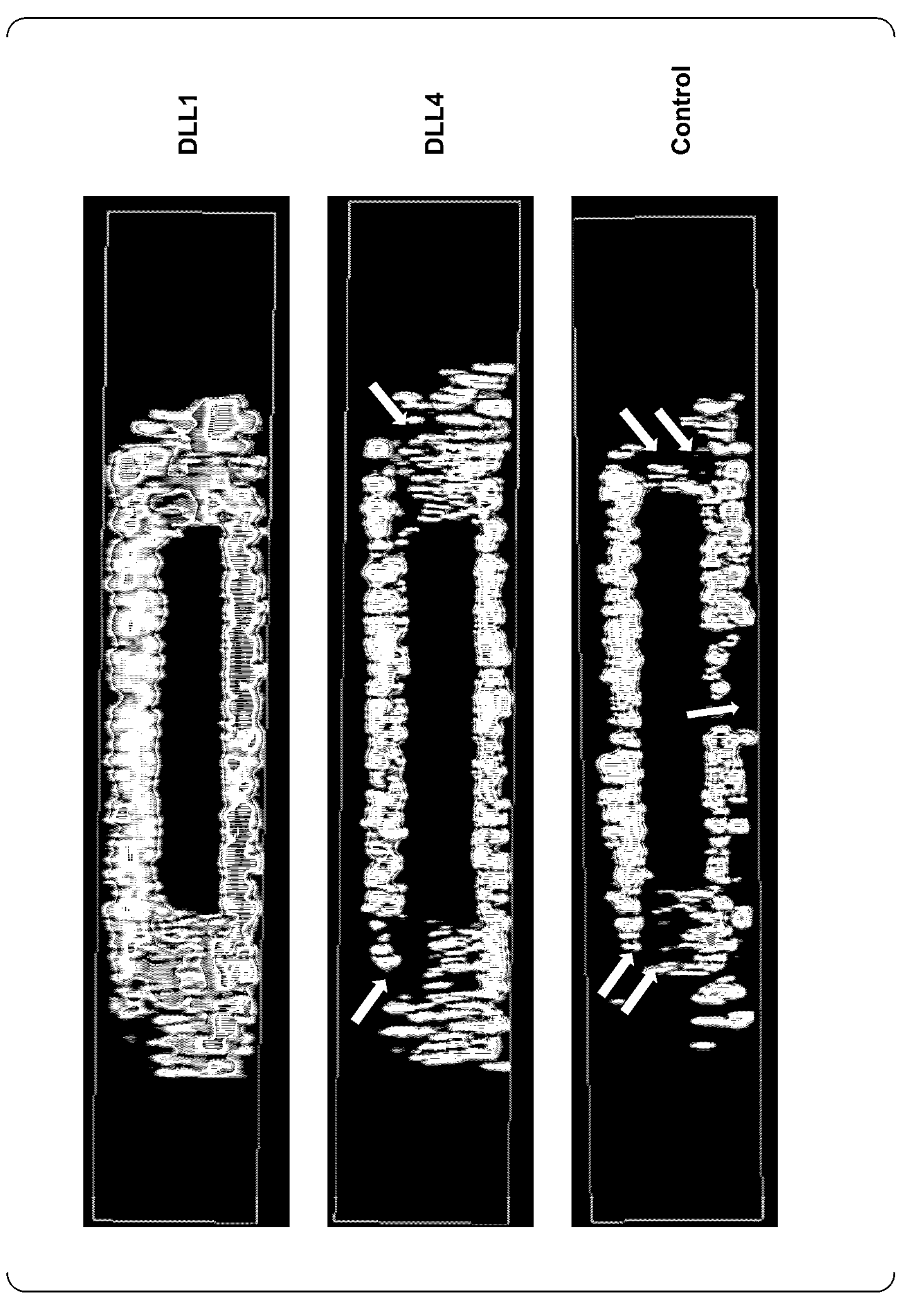
FIG. 18 shows fluorescence microscopic images of cross sections of microfluidic devices in Experimental Example 5.

FIG. 18 shows each of fluorescence microscopic images of cross sections of the microfluidic devices. In FIG. 18, each arrow indicates a region in which the GFP-expressing HuCCT1 cells are not present, and "Control" indicates the results in the absence of DLL1 and DLL4.

As a result, it was revealed that the addition of DLL1 or DLL4 to the culture medium accelerates the formation of the tubular bile duct-like structure.

Experimental Example 6

[Comparison of Gene Expression Levels in Intrahepatic Bile Duct Chip and Blood Vessel Chip]

GFP-expressing HuCCT1 cells were seeded in the lower layer flow path of the microfluidic device, and after 4 days, PHH was seeded in the upper layer flow path of the microfluidic device to produce an intrahepatic bile duct chip. In addition, GFP-expressing HUVEC was seeded in the lower layer flow path of the microfluidic device, and after 4 days, PHH was seeded in the upper layer flow path of the microfluidic device to produce a blood vessel chip. Subsequently, after co-culturing for one day, the gene expression levels of the liver markers (ALB, AAT, CYP3A4, CYP7A1, BSEP, and MRP2), the bile duct cell markers (AQP, KRT19), and the endothelial markers (CDHS, PECAM, and SELE) were measured by quantitative RT-PCR.

Figure 19:
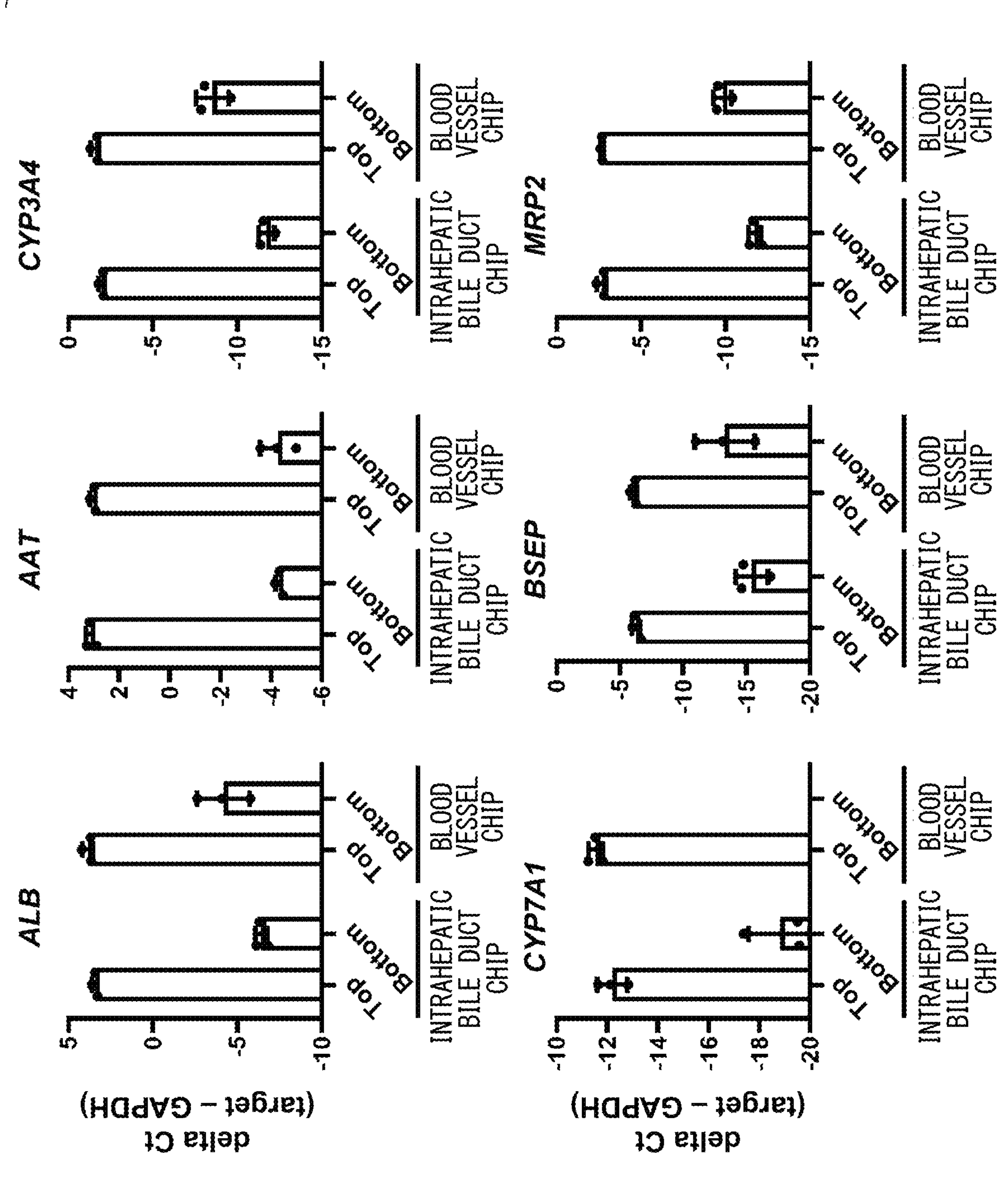
FIG. 19 shows graphs showing results of quantitative RT-PCR of liver markers in Experimental Example 6.
Figure 20:
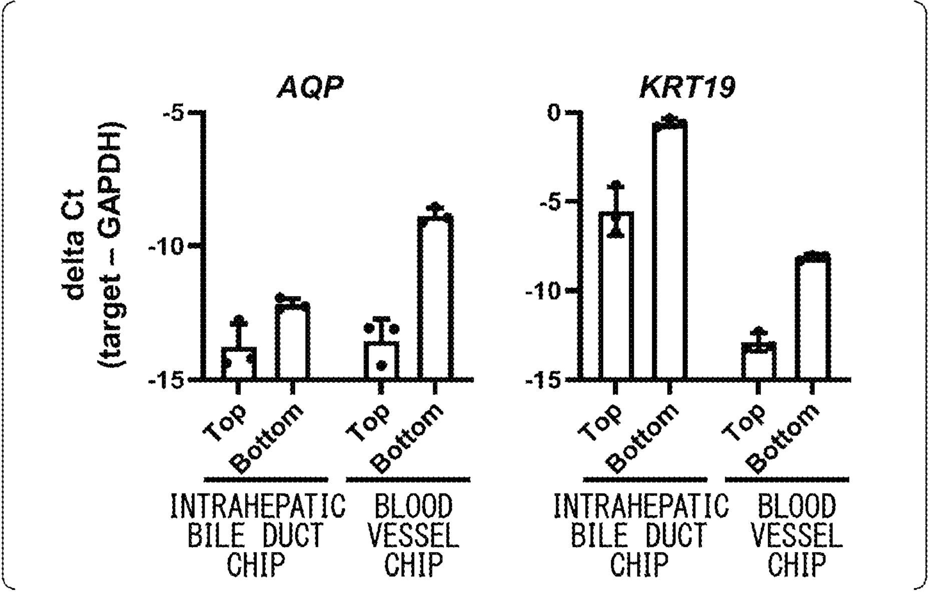
FIG. 20 shows graphs showing results of quantitative RT-PCR of bile duct cell markers in Experimental Example 6.
Figure 21:
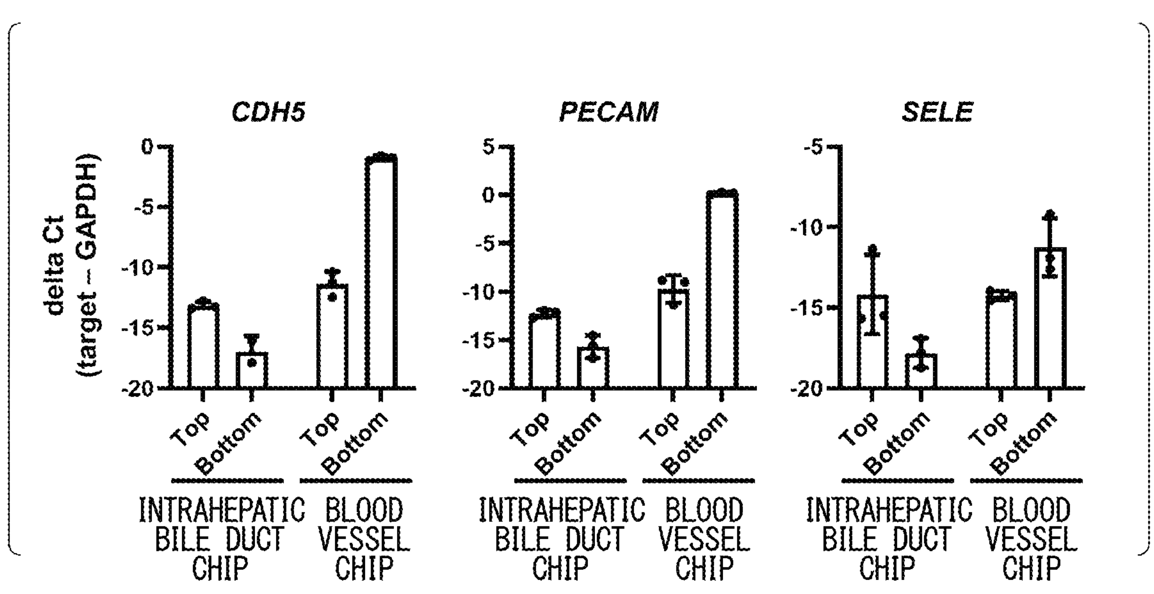
FIG. 21 shows graphs showing results of quantitative RT-PCR of endothelial markers in Experimental Example 6.

FIG. 19 shows graphs showing results of the quantitative RT-PCR of the liver markers. FIG. 20 shows graphs showing results of the quantitative RT-PCR of the bile duct cell markers. FIG. 21 shows graphs showing results of the quantitative RT-PCR of the endothelial markers. In FIGS. 19 to 21, "Top" indicates the results for cells in the upper layer flow path, and "Bottom" indicates the results for cells in the lower layer flow path.

Experimental Example 6

[Culturing of Human Hepatocyte in Microfluidic Device]

Human hepatocytes cultured in a microfluidic device were compared with human hepatocytes cultured on a polystyrene plate. Table 5 below shows the results of comparing the number of cells, the seeding area, the cell density, the volume of the culture medium, and the RNA yield in the polystyrene plate and the microfluidic device.

TABLE 5

| | Polystyrene plate | Microfluidic device |
|---|---|---|
| Material | Polystyrene | Polydimethylsiloxane |
| Coating | TYPE I COLLAGEN | TYPE I COLLAGEN |
| Number of cells | $3.3 \times 10^4$ | $5 \times 10^4$ |
| Area ($cm^2$) | 0.33 | 0.22 |
| Cell density (cells/$cm^2$) | $1.0 \times 10^5$ | $2.3 \times 10^5$ |
| Volume of culture medium (μL) | 100 | Upper layer: 200, Lower layer: 200 |
| RNA yield (ng) | 822 | 830 |

Figure 22:
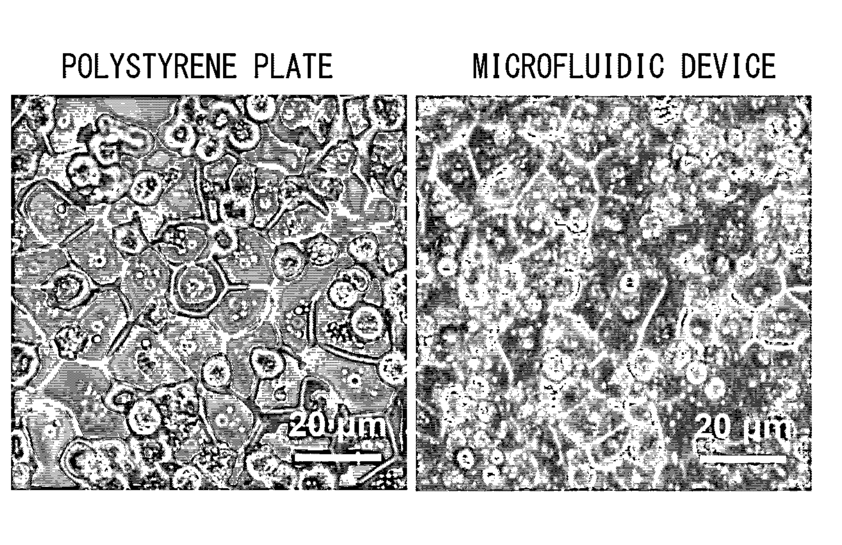
FIG. 22 shows phase contrast images of PHH cultured on a PET membrane of a microfluidic device and PHH cultured on a polystyrene plate in Experimental Example 6.

The PHH seeded in the microfluidic device was adhered to the PET membrane. FIG. 22 shows phase contrast images of the PHH cultured on the PET membrane of the microfluidic device and the PHH cultured on the polystyrene plate.

Figure 23:
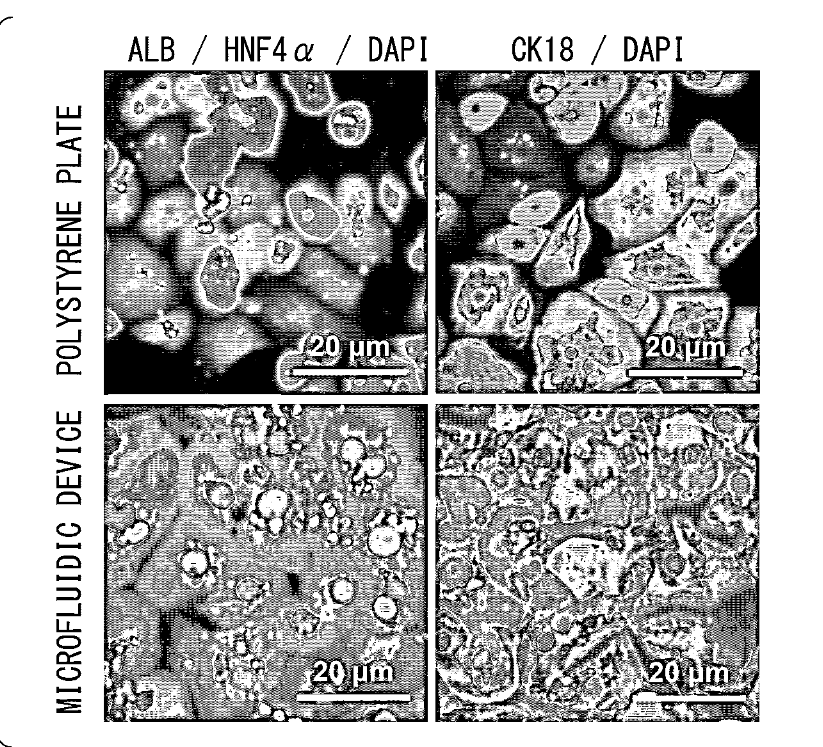
FIG. 23 shows fluorescence microscopic images showing results of immunochemical staining in Experimental Example 6.

Subsequently, the PHH cultured on the polystyrene plate and the PHH cultured in the microfluidic device were analyzed according to immunochemical staining, and the expressions of ALB, HNF4α, and CK18 were detected. The nuclei were stained with DAPI. FIG. 23 shows fluorescence microscopic images showing results of immunochemical staining. As a result, strong expressions of ALB and CK18 due to PHH were observed under any of the conditions.

Figure 24:
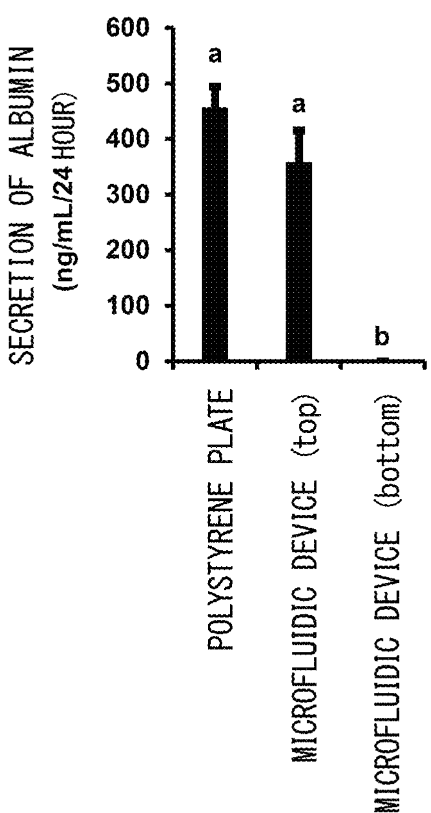
FIG. 24 is a graph showing results of measuring a secretion amount of albumin in Experimental Example 6.

Subsequently, the albumin secretion, due to the PHH cultured on the polystyrene plate and the PHH cultured on the microfluidic device, was measured according to ELISA. FIG. 24 is a graph showing results of measuring a secretion amount of albumin. In FIG. 24, "top" indicates the results for the upper layer flow path of the microfluidic device, and "bottom" indicates the results for the lower layer flow path of the microfluidic device. In addition, the values are indicated as average value±standard deviation (n=3). Different letters indicate that there is a significant difference at $p<0.05$.

As a result, the amount of human albumin secreted into the culture medium recovered from the upper layer flow path of the microfluidic device was approximately equal to the amount of human albumin secreted into the culture medium recovered from the polystyrene plate. Although the estimated diameter (about 6 nm) of human albumin was smaller than the pore size (3 μm) of the PET membrane, the human albumin was not detected from the lower layer flow path of the microfluidic device.

These results indicate that the PHH cultured in the microfluidic device maintains the hepatic function similar to the PHH cultured on the polystyrene plate in the related art.

Experimental Example 7

[Examination of Drug Absorption in Microfluidic Device without PHH]

It was examined whether or not five drugs generally used in the measurement of the CYP activity (midazolam (MDZ), diclofenac (DIC), phenacetin (PHE), bufuralol (BUF), and S-mephenytoin (MPHT) were absorbed in the microfluidic device.

Figure 25:
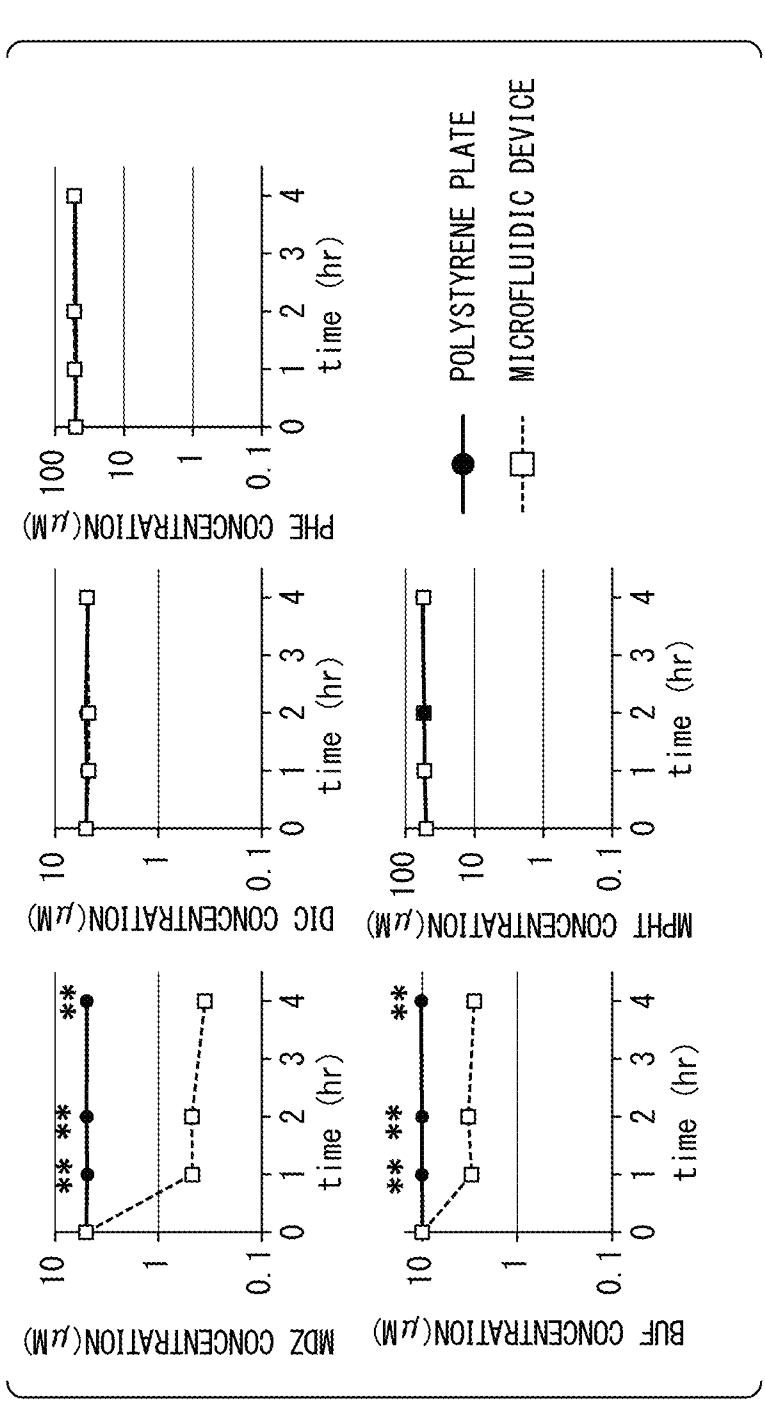
FIG. 25 shows graphs showing results of quantifying drugs in Experimental Example 7.

A culture medium containing MDZ, DIC, PHE, BUF, or MPHT was added to a microfluidic device or a polystyrene plate. Subsequently, 1, 2, and 4 hours after the addition of the drugs, the amounts of these drugs were quantified with LC-MS/MS. FIG. 25 shows graphs showing results of quantifying each of the drugs.

In addition, since the CYP activity is defined by the rate of metabolite formation, the diclofenac absorption of drug metabolites (1-hydroxymidazolam (1OH-MDZ), 4-hydroxy diclofenac (4OH-DIC), acetaminophen (APAP), 1-hydroxybufuralol (1OH-BUF), and 4-hydroxymephenytoin (4OH-MPHT) was also evaluated.

A culture medium containing APAP (a CYP1A2 metabolite), 1OH-MDZ (a CYP3A4 metabolite), 4OH-DIC (a CYP2C9 metabolite), 4OH-MPHT (a CYP2C19 metabolite), or 1OH-BUF (a CYP2D6 metabolite) was added to a microfluidic device or a polystyrene plate. Subsequently, 1, 2, and 4 hours after the addition of the drugs, the amounts of these drugs were quantified with LC-MS/MS. FIG. 26 shows graphs showing results of quantifying each of the drugs.

As a result, MDZ, which is a substrate of CYP3A4, and BUF, which is a substrate of CYP2D6, were absorbed in the microfluidic device. The concentrations of MDZ and BUF decreased to 9.5% and 30% of each of the initial concentrations thereof 1 hour after the injection into the microfluidic device. The MDZ metabolite (1OH-MDZ) was also absorbed in the PDMS device, whereas the BUF metabolite (1OH-BUF) was not absorbed therein. The concentrations of MDZ, BUF, and 1OH-MDZ were constant during the observation period (1 to 4 hours).

These results indicate that the rate of absorption into the microfluidic device may differ between the drugs and the metabolites thereof.

Figure 27:
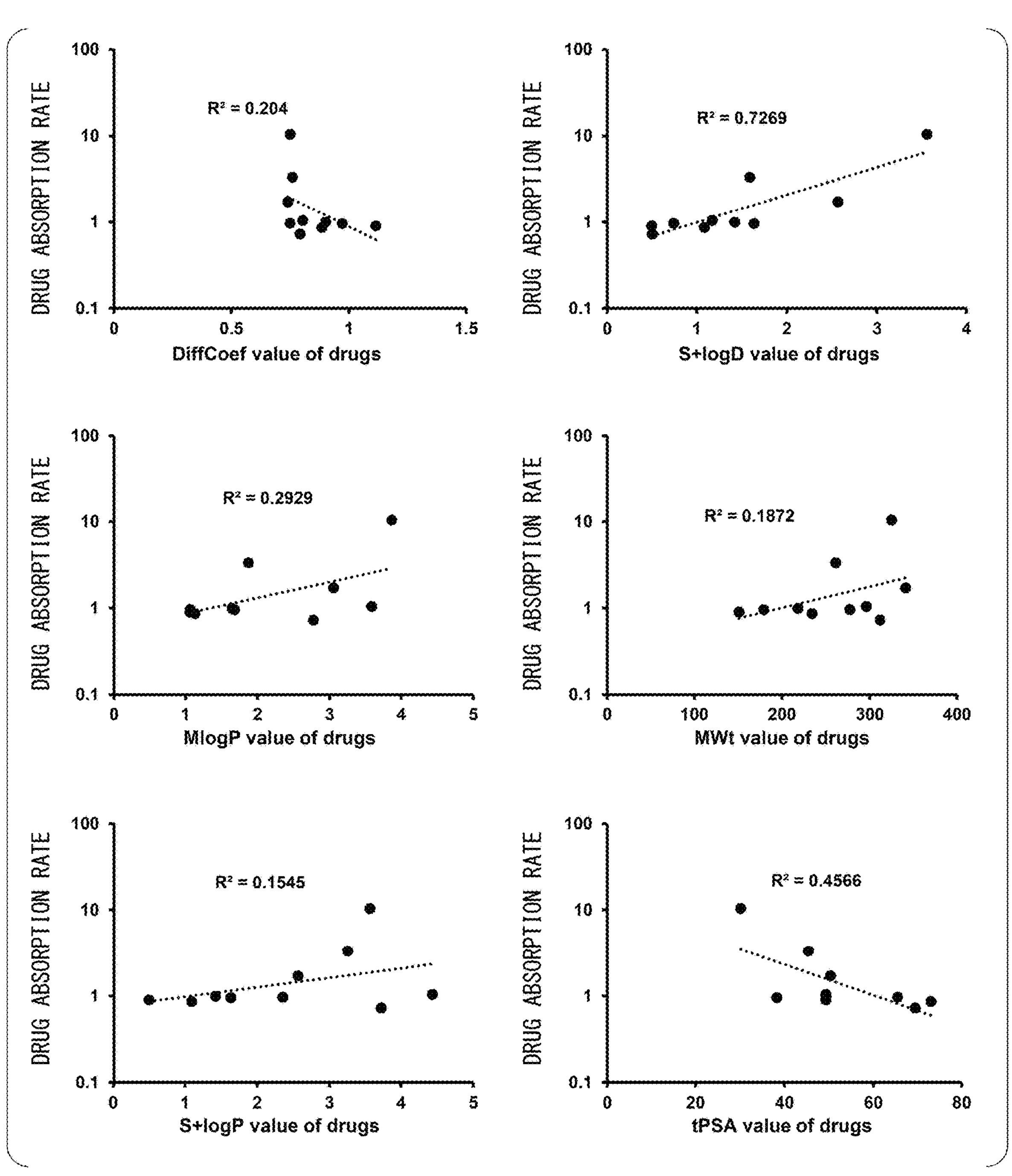
FIG. 27 shows graphs showing results of calculating a correlation coefficient $R^2$ value between a drug absorption rate and physicochemical characteristics of drugs in Experimental Example 7.

Subsequently, it was examined whether the absorption of the drugs and metabolites could be predicted by the relative physicochemical characteristics between the microfluidic device and the polystyrene plate. The drug absorption rate between the microfluidic device and the polystyrene plate was calculated. Subsequently, a correlation coefficient $R^2$ value between the drug absorption rate and the physicochemical characteristics (DiffCoef, M Log P, S+Log P, S+log D, MWt, and tPSA) of the drugs was calculated. The results are shown in Table 6 below and FIG. 27.

TABLE 6

| | DiffCoef | MlogP | S + logP | S + logD | MWt | tPSA |
|---|---|---|---|---|---|---|
| Drug absorption rate (Microfluidic device/Polystyrene plate) | $R^2$ = 0.2268 | $R^2$ = 0.2322 | $R^2$ = 0.1305 | $R^2$ = 0.713 | $R^2$ = 0.172 | $R^2$ = 0.4847 |

In addition, using a MedChem Designer 5.5, the diffusion coefficient (DiffCoef), the distribution coefficient (M Log P, S+Log P, and S+log D), the molecular weight (MWt), and the topological polar surface area (TPSA) of each drug were calculated. The results are shown in Table 7 below.

TABLE 7

| Drug | DiffCoef | MlogP | S + logP | S + logD | MWt | tPSA | Drug absorption rate |
|---|---|---|---|---|---|---|---|
| Midazolam | 0.75 | 3.864 | 3.563 | 3.562 | 325.775 | 30.18 | 10.41468887 |
| Diclofenac | 0.804 | 3.582 | 4.434 | 1.173 | 296.155 | 49.33 | 1.042613078 |
| Phenacetin | 0.972 | 1.68 | 1.635 | 1.635 | 179.22 | 38.33 | 0.956932989 |
| Bufuralol | 0.76 | 1.874 | 3.256 | 1.591 | 261.366 | 45.4 | 3.327065076 |
| S-mephenytoin | 0.901 | 1.649 | 1.423 | 1.423 | 218.257 | 49.41 | 0.989656846 |
| 1-hydroxymidazolam | 0.741 | 3.056 | 2.569 | 2.569 | 341.774 | 50.41 | 1.714399273 |
| 4-hydroxy diclofenac | 0.793 | 2.774 | 3.718 | 0.508 | 312.154 | 69.56 | 0.725038117 |
| Acetaminophen | 1.114 | 1.06 | 0.502 | 0.501 | 151.166 | 49.33 | 0.898711463 |
| 1-hydroxybufuralol | 0.75 | 1.066 | 2.355 | 0.747 | 277.366 | 65.63 | 0.964767185 |
| 4-hydroxymephenytoin | 0.885 | 1.129 | 1.093 | 1.086 | 234.256 | 73.13 | 0.863272529 |

As a result, it was revealed that the drug absorption rate between the microfluidic device and the polystyrene plate correlates with the S+log D value ($R^2$=0.71). In addition, it was revealed that except for BUF, drugs with S+log D<2 are hardly absorbed in the microfluidic device.

Experimental Example 9

[Examination of CYP Induction and Metabolism in PHH Cultured in Microfluidic Device]

It was examined whether the PHH cultured in the microfluidic device or the polystyrene exhibits a CYP inducibility. PHH was seeded in each of a microfluidic device and a polystyrene plate and cultured for 24 hours. Subsequently, the cultured PHH was treated with 50 μM omeprazole, 500 μM phenobarbital, or 20 nM rifampicin for 48 hours. It is known that omeprazole is a CYP1A2-inducing agent, phenobarbital is a CYP2B6-inducing agent, and rifampicin is a CYP3A4-inducing agent. Subsequently, the expression level of each CYP gene was measured by quantitative RT-PCR. Cells treated with DMSO (final concentration: 0.1%) were used as a control.

Figure 28:
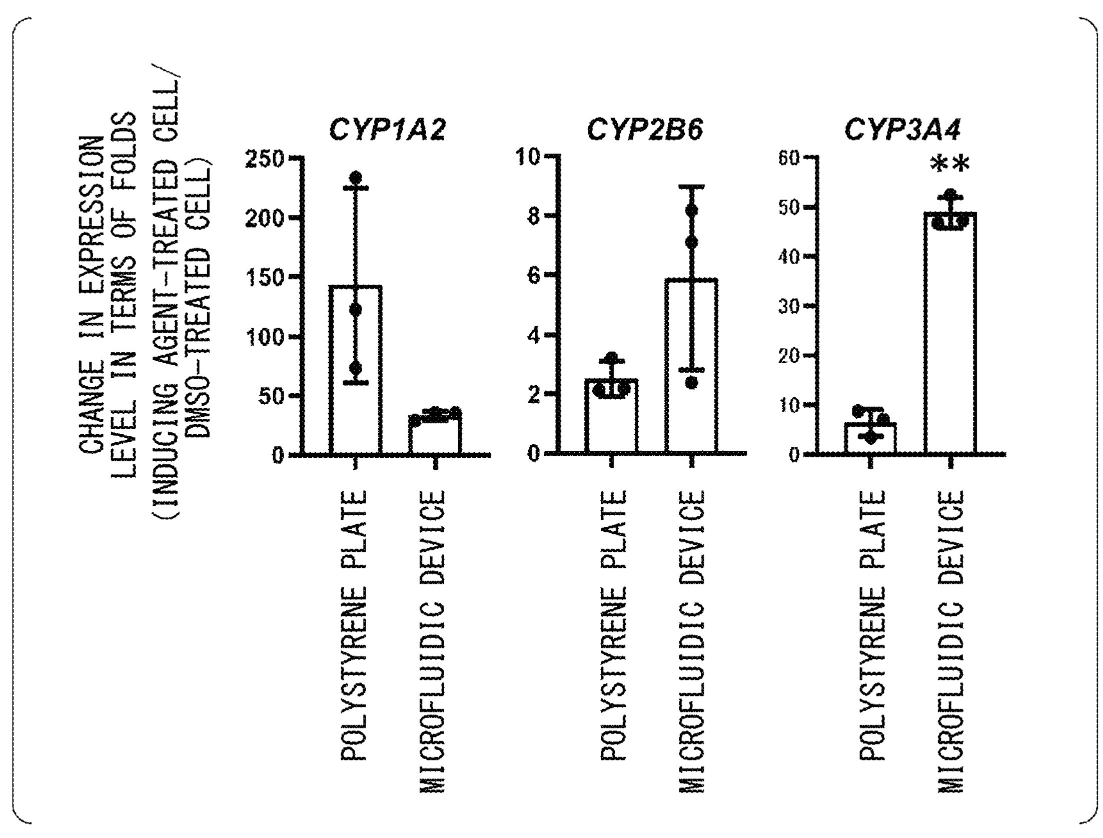
FIG. 28 shows graphs showing results of quantitative RT-PCR in Experimental Example 9.

FIG. 28 shows graphs showing results of quantitative RT-PCR. In FIG. 28, the vertical axis of the graph indicates a change in expression level in terms of folds in a case where the gene expression level in the PHH treated with DMSO is set to 1. "**" indicates that there is a significant difference at $p<0.01$. As a result, it was confirmed that the expression levels of CYP1A2, CYP2B6, and CYP3A4 are induced in both the microfluidic device and the polystyrene plate.

The induction of CYP3A4 by the rifampicin treatment in the microfluidic device was strong as compared with the induction in the polystyrene plate, whereas there was no significant difference in the induction of CYP1A2 and CYP2B6.

These results indicate that the CYP inducibility of the cultured PHH is different between the PDMS device and the PS plate. A possibility was conceived that there is a difference in the absorption level of the CYP-inducing substance between the two systems, which may be the cause of the different CYP inducibility.

Subsequently, the drug metabolic activities of the PHH cultured in the PDMS device and the PS plate were compared. First, PHH was treated with each of MDZ, DIC, PHE, BUF, and MPHT, which are substrates of CYP3A4, CYP2C9, CYP1A2, CYP2D6, and CYP2C19. Subsequently, after 1, 2, and 4 hours, the amounts of the metabolites (OH-MDZ, 4OH-DIC, APAP, 1OH-BUF, and 4OH-MPHT) generated in the culture medium were measured by LC-MS/MS.

FIG. 29 shows graphs showing results of measuring the fluorescence intensity of each of the metabolites. In FIG. 29, "*" indicates that there is a significant difference at $p<0.05$, and "**" indicates that there is a significant difference at $p<0.01$. The data is indicated as average value±standard deviation (n=3).

As a result, the formation rates of APAP (a CYP1A2 metabolite), 1OH-MDZ (a CYP3A4 metabolite), and 1OH-BUF (a CYP2D6 metabolite) in the PHH cultured in the microfluidic device were similar to those in the PHH cultured on the polystyrene plate.

As described above, since MDZ and BUF are easily absorbed in the microfluidic device, the amount of the metabolite of the PHH cultured in the microfluidic device was smaller than the amount of the metabolite of the PHH cultured in the polystyrene plate. However, the clearance defined by dividing the rate of drug metabolite formation by the concentration of the drug in the culture medium showed no difference (FIG. 29).

The formation rates of 4OH-DIC (a CYP2C9 metabolite) and 4OH-MPHT (a CYP2C19 metabolite) by the PHH cultured in the microfluidic device were significantly lower than those by the PHH cultured on the PS plate. This difference was conceived to be due to the fact that the microfluidic device reduced the activity of CYP2C9 and CYP2C19.

Subsequently, the CYP3A-mediated metabolic activity of atorvastatin (ATV) in PHH was examined. It is known that ATV is incorporated by OATP1B, which is a liver transporter, and subsequently metabolized by CYP3A.

PHH was seeded on a microfluidic device and a polystyrene plate and cultured for 24 hours. Subsequently, the PHH was cultured in a culture medium containing ATV for 1, 2, and 4 hours, and the concentrations of 2-hydroxyatorvastatin (2OH-ATV) and ATV were measured with LC-MS/MS. In addition, for comparison, a specimen obtained by adding SKF-525A, which is a pan-CYP inhibitor, to a culture medium was also prepared.

Figure 30:
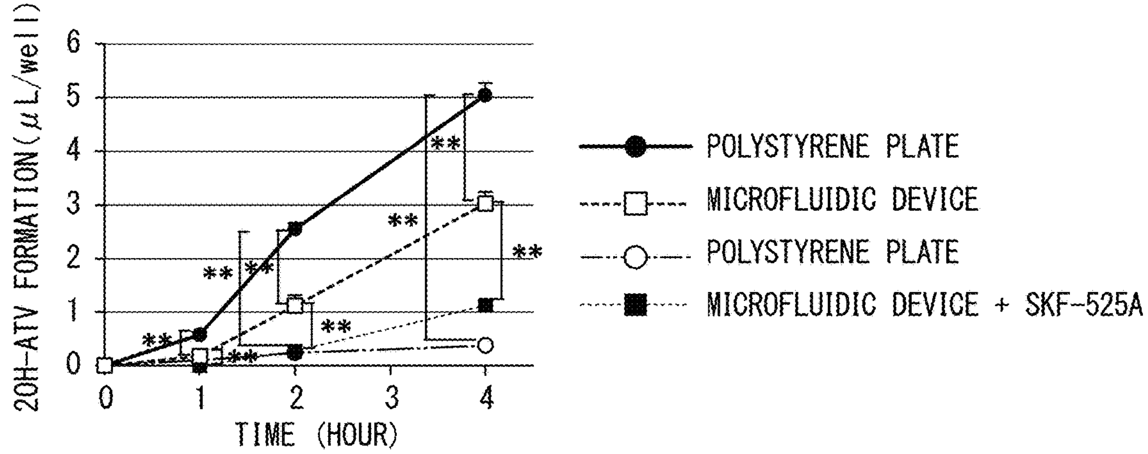
FIG. 30 is a graph showing results of measuring 2-hydroxyatorvastatin (2OH-ATV) in Experimental Example 9.
Figure 31:
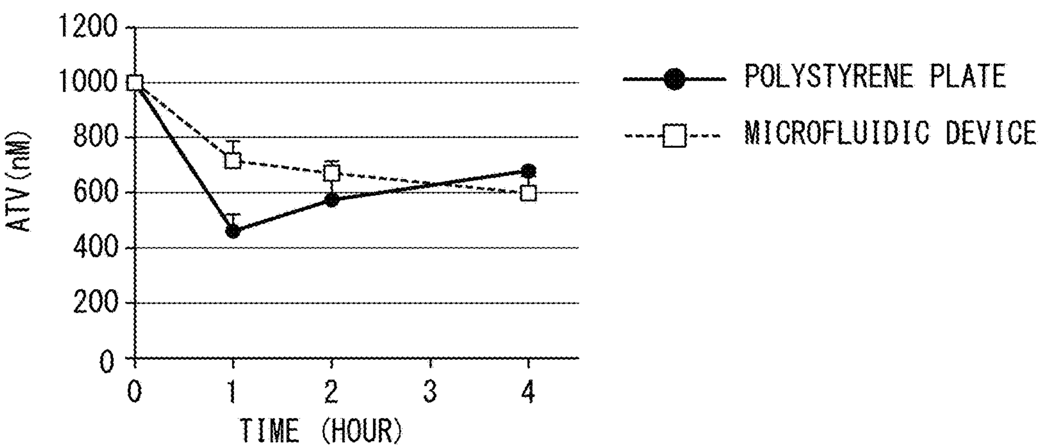
FIG. 31 is a graph showing results of measuring atorvastatin (ATV) in Experimental Example 9.

FIG. 30 is a graph showing results of measuring 2OH-ATV. In FIG. 30, "" indicates that there is a significant difference at $p<0.01$. In addition, FIG. 31 is a graph showing results of measuring ATV. In FIGS. 30 and 31**, the data is indicated as average±standard deviation (n=3).

As a result, the formation of 2OH-ATV was observed in a time-dependent manner and was significantly reduced by a treatment with SKF-525A. On the other hand, the concentration of ATV in the culture medium was similar between the microfluidic device and the polystyrene plate.

Summarizing the above results, since there is a difference in the absorption of the CYP substrate and the CYP metabolite between the microfluidic device and the polystyrene plate, it is necessary to carefully evaluate the drug metabolic ability of the PHH cultured in the microfluidic device.

The PHH cultured in the microfluidic device maintained the activity of CYP3A4, CYP1A2, and CYP2D6, whereas the activity of CYP2C9 and CYP2C19 was significantly decreased for an unknown reason.

In addition, the CYP3A activity was maintained in the PHH cultured in the microfluidic device, whereas the formation rate of 2OH-ATV was partially reduced. Considering that the rate-determining step of liver clearance of ATV is a hepatic incorporation process, this result suggests the possibility that the transport activity of OATP1B is reduced in the microfluidic device.

Experimental Example 10

[Examination of Drug Responsiveness of PHH Cultured in Microfluidic Device]

The drug responsiveness of the PHH cultured in the microfluidic device and the polystyrene plate was evaluated. PHH was treated with acetaminophen (APAP), which is known to cause drug-induced liver damage at a high concentration, in order to investigate whether or not drug-induced liver damage can be evaluated in PHH cultured in a microfluidic device. PHH was seeded in a microfluidic device or a polystyrene plate and cultured for 24 hours. Subsequently, the PHH was exposed to 10 mM acetaminophen for 4 days. Subsequently, cell viability was measured according to a WST-8 assay.

Figure 32:
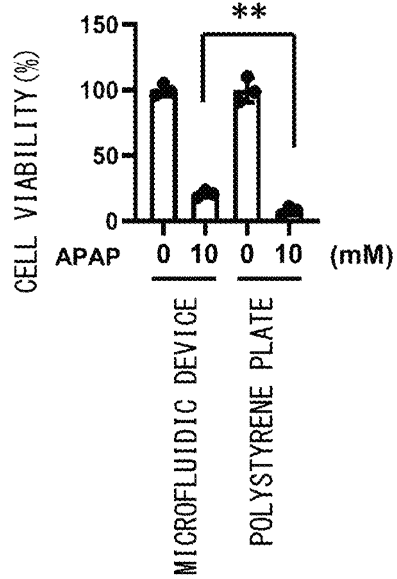
FIG. 32 is a graph showing results of measuring cell viability in Experimental Example 10.

FIG. 32 shows the standardized cell viability based on the cells treated with a vehicle alone. The data is indicated as average value±standard deviation (n=3). In FIG. 32, "APAP" indicates acetaminophen, and "**" indicates that there is a significant difference at $p<0.01$.

As a result, the cell viability of the PHH cultured in the microfluidic device was significantly lower than the cell viability of PHH cultured in the polystyrene plate. This result indicates that the microfluidic device has a high sensitivity to the APAP-induced liver damage.

Figure 33:
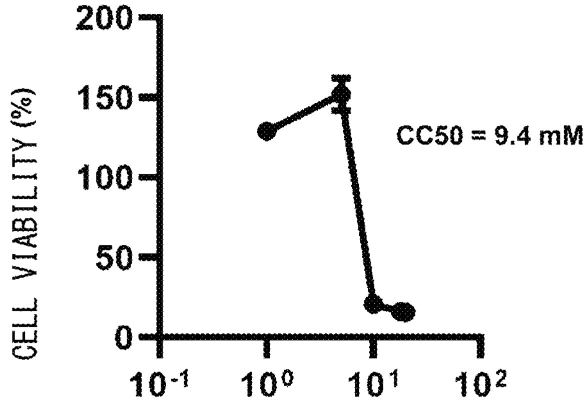
FIG. 33 is a graph showing results of measuring cell viability in Experimental Example 10.

Subsequently, the hepatotoxicity of PHH due to acetaminophen was examined. The PHH cultured on the polystyrene plate was exposed to acetaminophen at various concentrations for 4 days. Subsequently, cell viability was measured according to a WST-8 assay. FIG. 33 shows the standardized cell viability based on the cells treated with a vehicle alone. The data is indicated as average value±standard deviation (n=3). As a result, a 50% cytotoxicity concentration (CC50) was calculated to be 9.4 mM.

Subsequently, a change in bile acid signaling upon drug exposure was examined. Specifically, PHH was treated with chenodeoxycholic acid (CDCA), which is an FXR ligand, and GW4046, which is a synthetic ligand.

PHH was exposed to 100 μM chenodeoxycholic acid (CDCA) and 2.5 μM GW4046 for 72 hours. CDCA is a FXR ligand and GW4046 is a synthetic ligand.

Figure 34:
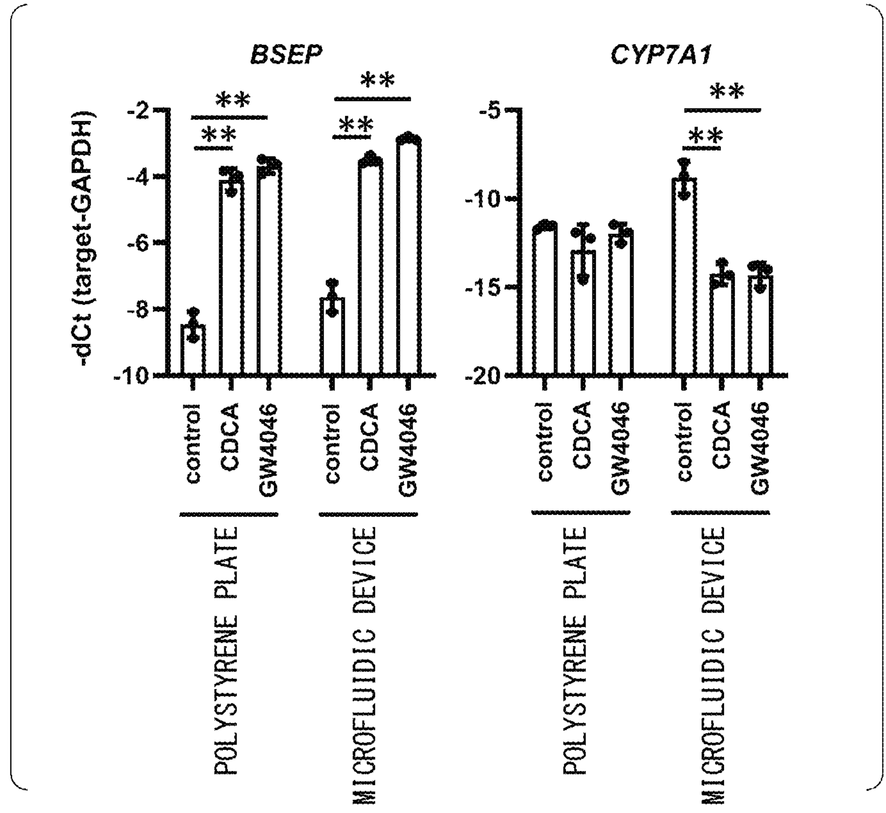
FIG. 34 shows graphs showing results of quantitative RT-PCR in Experimental Example 10.

Subsequently, the gene expression levels of BSEP and CYP7A1 were measured by quantitative RT-PCR. FIG. 34 shows graphs showing results of quantitative RT-PCR. In FIG. 34, "*" indicates that there is a significant difference at $p<0.01$.

As a result, the gene expression level of BSEP, which is a bile acid excretion transporter, was increased in both the PHH cultured in the microfluidic device and the PHH cultured on the polystyrene plate. Interestingly, the gene expression level of CYP7A1, which is the rate-determining enzyme of the hepatic bile acid synthesis, was decreased only in the microfluidic device.

These results indicate that the response to the FXR ligand by the PHH cultured in the microfluidic device is higher than that of the PHH cultured on the polystyrene plate.

Subsequently, the cellular response of the PHH cultured in the microfluidic device and the polystyrene plate to a recombinant protein was examined. Specifically, PHH was treated with transforming growth factor-β1 (TGF-β1), which is one of the causative factors of hepatic fibrosis. The PHH was exposed to 100 ng/mL TGF-β1 for 48 hours.

Subsequently, the amount of TGF-β1 in the cell culture supernatant was measured according to ELISA.

Figure 35:
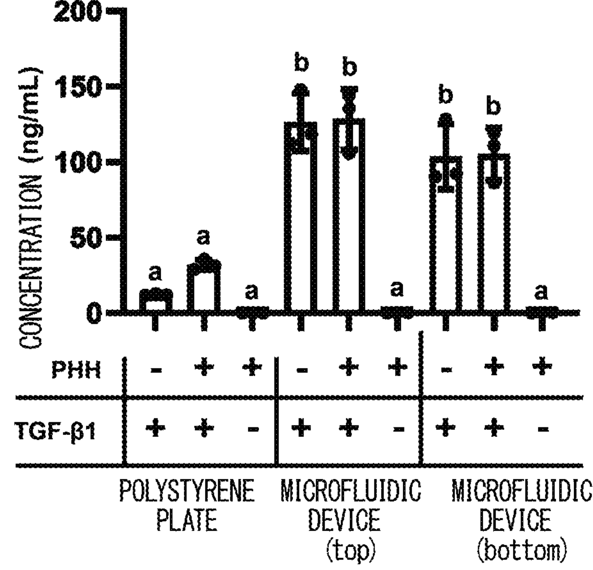
FIG. 35 is a graph showing results of quantifying TGF-β1 according to ELISA in Experimental Example 10.

FIG. 35 is a graph showing the results of ELISA. In FIG. 35, "top" indicates the results for the upper layer flow path, and "bottom" indicates the results for the lower layer flow path. In addition, groups that do not share the same character are significantly different from each other ($p<0.05$). As a result, it was shown that the microfluidic device has not allowed the adsorption of TGF-β1. On the other hand, the polystyrene plate allowed the adsorption of TGF-β1.

Subsequently, the gene expression levels of ACTA2, COL1A1, and TIMP1, which are fibrosis markers, were measured by quantitative RT-PCR.

Figure 36:
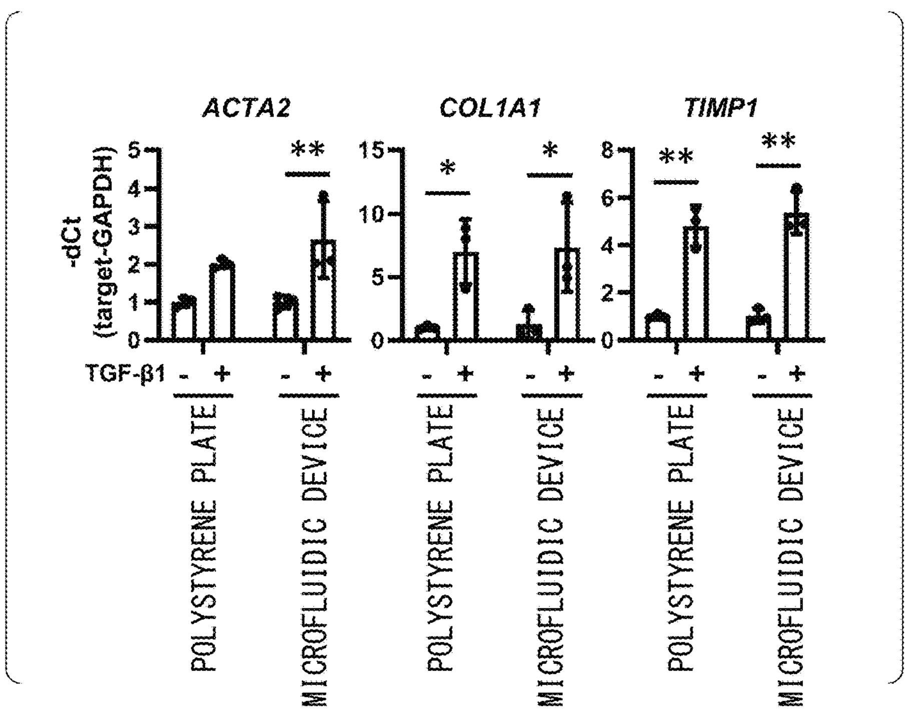
FIG. 36 shows graphs showing results of quantitative RT-PCR in Experimental Example 10.

FIG. 36 shows graphs showing results of quantitative RT-PCR. In FIG. 36, the vertical axis indicates a relative value in a case where the gene expression level in the cells (control) treated with phosphate buffered saline (PBS) is set to 1. In addition, "*" indicates that there is a significant difference at $p<0.05$, and "**" indicates that there is a significant difference at $p<0.01$. The data is indicated as average value±standard deviation (n=3).

As a result, it was shown that the gene expression levels of ACTA2, COL1A1, and TIMP1 in PHH are increased by the TGF-β1 treatment regardless of whether being the microfluidic device or the polystyrene plate.

Subsequently, the gene expression level of TGF-β type II receptor (TGFBR2) was measured. PHH was seeded in a microfluidic device and a polystyrene plate and cultured for 24 hours. Subsequently, the gene expression level of TGFBR2 was measured by quantitative RT-PCR.

Figure 37:
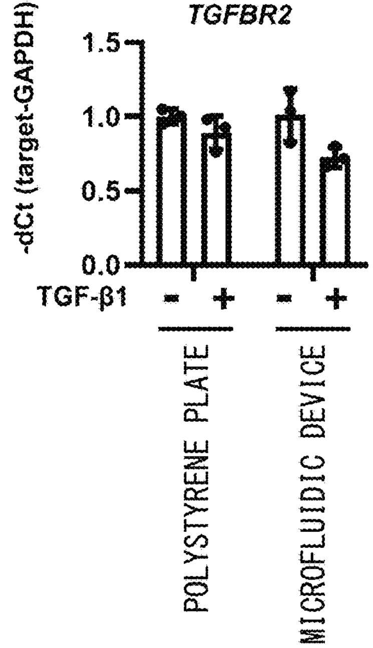
FIG. 37 shows graphs showing results of quantitative RT-PCR in Experimental Example 10.

FIG. 37 shows graphs showing results of quantitative RT-PCR. In FIG. 37, the vertical axis indicates a relative value in a case where the gene expression level in the PHH immediately after thawing is set to 1. The data is indicated as average value±standard deviation (n=3). As a result, it was shown that the TGFBR2 gene expression level is not changed by the TGF-β1 treatment.

Accordingly, both the microfluidic device and the polystyrene plate can be used to evaluate the fibrosis caused by TGF-β1. From the above results, it was confirmed that both the PHH cultured in the microfluidic device and the PHH cultured on the polystyrene plate retain the ability to respond to drugs and recombinant proteins.

Subsequently, the correlation between the drug responsiveness of the PHH cultured in the microfluidic device and the physicochemical characteristics of the drugs was searched. As described above, the drug absorption rate between the microfluidic device and the polystyrene plate correlated with the S+log D value, whereas the drug responsiveness of PHH did not correlate with the physicochemical characteristics. This may be because the hepatic characteristics of PHH are slightly changed by culturing with the microfluidic device. These results indicate that it is difficult to predict the drug reactivity of the liver chip.

INDUSTRIAL APPLICABILITY

According to the present invention, it is possible to provide a bile duct chip having a tubular bile duct-like structure.

REFERENCE SIGNS LIST

200: Bile duct chip
210: membrane
220, 230: Flow path
221,231: Substrate
222: Bile duct epithelial cell
232: Second cell.

The invention claimed is:

1. A bile duct chip comprising:

a membrane comprising a first surface and a second surface opposite the first surface and enabling substances to move from the first surface to the second surface;

a first substrate having a first recessed part forming a first flow path having an inner wall surface;

a second substrate having a second recessed part forming a second flow path; and first biological cells disposed in the inner wall surface of the first recessed part and forming a tubular structure, wherein the first biological cells are bile duct epithelial cells, the membrane is stacked between the first substrate and the second substrate, the first recessed part has a first opening portion facing the first surface, the second recessed part has a second opening portion facing the second surface, the first surface forms a first part of the first flow path, the second surface forms a second part of the second flow path, and the first flow path and the second flow path are in fluid communication through the membrane.

2. The bile duct chip according to claim 1, further comprising second biological cells disposed in the second flow path, wherein the second biological cells are adjacent to the first biological cells across the membrane.

3. The bile duct chip according to claim 2, wherein the second biological cells are liver cells or intestinal cells or a combination thereof.

4. The bile duct chip according to claim 3, wherein the second biological cells are the liver cells, and the tubular structure is an intrahepatic bile duct model.

5. A method of preparing the bile duct chip according to claim 1, the method comprising introducing a culture medium containing a lumenization factor into the first flow path.

6. The method according to claim 5, wherein the lumenization factor is Delta Like Canonical Notch Ligand 1 (DLL 1) or Delta Like Canonical Notch Ligand 4 (DLL4) or a combination thereof.

7. The method according to claim 6, wherein the lumenization factor consists of the Delta Like Canonical Notch Ligand 1 (DLL 1).

8. The method according to claim 5, further comprising: seeding second biological cells in the second flow path.

9. The method according to claim 8, wherein the second biological cells are liver cells or intestinal cells or a combination thereof.

10. The method according to claim 9, wherein the second biological cells are the liver cells, and the tubular structure is an intrahepatic bile duct model.

11. A method of evaluating bile acid kinetics using the bile duct chip according to claim 1, the method comprising:

adding an amount of a test substance into the first flow path or adding an amount of the test substance into the second flow path, wherein the second flow path comprises liver cells; and measuring bile acid level in the first flow path, or measuring the bile acid level in the second flow path, or measuring a gene expression level, or measuring a protein level, the gene and the protein associated with bile acid kinetics in bile duct epithelial cells or the gene expression level and the protein level associated with bile acid kinetics in the liver cells.

12. The method according to claim 11, wherein the bile acid kinetics is associated with an in vivo compound other than bile acid, with a drug, with a pathogen, or with a bile acid.

* * * * *